(12) United States Patent
Kharbanda et al.

(10) Patent No.: US 6,602,500 B1
(45) Date of Patent: Aug. 5, 2003

(54) *PAENIBACILLUS POLYMYXA* STRAIN ATCC 202127 FOR BIOCONTROL OF BACTERIA AND FUNGI

(75) Inventors: Prem Dutt Kharbanda, Edmonton (CA); Richard Nigel Coleman, Vegreville (CA); Perrin Hudson Beatty, Edmonton (CA); Susan Elaine Jensen, Edmonton (CA); Jalpa P. Tewari, Edmonton (CA); Jian Yang, Edmonton (CA)

(73) Assignees: The Governors of the University of Alberta, Edmonton (CA); Alberta Research Council, Edmonton (CA)

( * ) Notice: Subject to any disclaimer, the term of this patent is extended or adjusted under 35 U.S.C. 154(b) by 0 days.

(21) Appl. No.: 09/700,486
(22) PCT Filed: May 20, 1999
(86) PCT No.: PCT/CA99/00426
§ 371 (c)(1), (2), (4) Date: Feb. 5, 2001
(87) PCT Pub. No.: WO99/59412
PCT Pub. Date: Nov. 25, 1999

(30) Foreign Application Priority Data

May 20, 1998 (GB) .............................................. 2238289

(51) Int. Cl.[7] ........................ A01N 25/00; A01N 63/00; C12N 1/00; C12N 1/20
(52) U.S. Cl. ................. 424/93.46; 424/405; 435/252.5; 435/838
(58) Field of Search ................................ 424/405, 93.1, 424/93.46; 435/822, 252.1, 252.5, 838

(56) References Cited

U.S. PATENT DOCUMENTS 3,923,978 A 12/1975 Nakalima
4,663,162 A 5/1987 Kado et al.
6,146,428 A * 11/2000 Kalum .......................... 8/401

FOREIGN PATENT DOCUMENTS

EP 0276132 7/1988

OTHER PUBLICATIONS

Keiji Kurusu and K. Ohba, New peptide antibiotics LI–F03, F04, F05, F07, and F08 Produced by Bacillus Polymyxa, The Journal of Antibiotics Nov. 1987.

P. Beatty, Purification and Partial characterization of an Antifungal Antibiotic Produced by Bacillus Polymyxa DKBI. American Society for Microbiology May 20, 1998.

* cited by examiner

*Primary Examiner*—David M. Naff
*Assistant Examiner*—Deborah K. Ware
(74) *Attorney, Agent, or Firm*—Bennett Jones LLP

(57) ABSTRACT

*Paenibacillus polymyxa* strain ATCC 202127 capable of producing a peptide antibiotic against fungi, and specifically Leptosphaeria spp. is disclosed. Further, mutants of said strain capable of producing the peptide are also disclosed. In addition, a method of controlling a fungal disease of a crop is disclosed. The method comprises applying an amount of the strain or mutants thereof to at least one of a medium for growing the crop, seeds of the crop prior to planting, and plants of the crop. The strain can also inhibit the growth of bacteria such as Micrococcus spp., Streptomyces spp. or Escherichia spp. The fungi which the strain or mutants thereof capable of producing the peptide are effective against include in addition to Leptosphaeria spp., the fungus selected from Sclerotinia spp., Rhizotonia spp., Pythium spp., Fusarium spp., Alternaria spp., Aspergillus spp., Sporobolomyces spp., Trichoderma spp., Penicillium spp. or Marasmius spp.

16 Claims, 14 Drawing Sheets

OPA08

GTGACGTAGG GTTAGGCGCG CATTTAGCGG ATCGGCATCC CCATGAATTC
AGTGGCGGGC AGCGTCAACG GATTGGCATA GCGAGAGCAC TGGCTATGAA
ACCGAAGCTC ATTGTTTGTG ATGAACCTGT ATCCGCGCTG GATGTGTCAA
TTCAGGCTCA GATTTGAAT TTGTTAAAGG AGCTTCAGCA GCAGTTCCAG
CTTACCTACA TTTTTATTGC CCACGGGTTG CCCTCCGTCA AGCATATTAG
CGACCGCATC GCGGTGATGT ACTTGGGCAA AATCGTGGAG CTTGCAGATC
GTGACGAGTT GTTTGCAAGA CCGCAACATC CGTATACAAA AGCATTGCTT
GAGGCAGTGC CTGTTCCTGA TCCGAGGTTG CGTATAAGAA CGGATCACAT
TGACGGGGGA AATCCCCAAT CCCGCCAATC CGCCTTCGGG CTGTACTTTT
CACACGCGTT GCCCCTATGC ACAAGAGATA TGCCGACTAC AGAGTCCATT
GCTCGAAGAG CATACTCCAG GACATATTGC TGCCTGTCAT TTTCCCCTGC
ATAAGCAGGT GGCTCAGGAA TAGATGAACT TTTGGAAGTA GGCGTTAACC
AAAAAAGGA GGCTACTCAT GAATAAACGA TCAATTGTAC CGGAGGATTT
GTACGGATAT CAGTGGATCA GTGATCCAC AATAAGCCCC GATGGAACGA
TTGCCTACGT CAC

OPA08

Figure 11. DNA sequence of probe P1-8.

PAENIBACILLUS POLYMYXA STRAIN ATCC 202127 FOR BIOCONTROL OF BACTERIA AND FUNGI

FIELD OF THE INVENTION

The present invention is directed toward a biocontrol agent and pesticide and, in particular, biocontrol agent and pesticide for inhibition of disease-causing fungi.

BACKGROUND OF THE INVENTION

Blackleg is a fungal disease of canola that is responsible for losses in crop yield and seed quality. The disease has spread throughout most of the Canadian prairies despite the use of fungicides and blackleg resistant canola cultivars. No successful inhibitor to the spread of blackleg exists, therefore another method of disease control is sought.

Canola is an economically important crop in Canada and considerable losses in seed quality and yield are seen every year due to fungal diseases such as blackleg. The canola cultivars presently grown show varying degrees of susceptibility to blackleg, and to date, there are also no varieties resistant to Sclerotinia white stem rot.

Canola is an important agricultural product in Canada, with a cash value of over $300 million per year in Alberta alone. In 1994 agronomists reported that the global consumption of vegetable oils is increasing by about 4% every year. To meet this global demand for canola oil Canada would need to grow 15% more than the 1994 acreage, and since that time there has been no abatement in the demand for canola oil. One of the major blocks to increasing the production of canola is the loss of crops to fungal diseases such as blackleg, Sclerotinia, Alternaria and Rhizoctonia. Much work has been done on developing blackleg disease tolerant canola cultivars. These new varieties help to improve the crop yield, however the canola cultivars are still not resistant to the fungal diseases. Some measure of control is achieved using chemical fungicides as a seed treatment, but newly emerged seedlings are still susceptible to disease. As a result, crop rotation on a four year cycle is an essential element in the control of blackleg disease, which further restricts the amount of canola which can be produced.

Fungal diseases also adversely affect other crops. As an example, fairy ring, caused by *Marasmius oreades*, is a common disease of turf grass.

Fungicidal seed treatments are used for chemical control of disease-causing fungus. However, single applications at the time of seeding do not provide sustained protection for the plants, and considerable losses can still occur before the crop reaches a stage of growth where some natural resistance has developed. Multiple fungicide applications are undesirable from both an economic and environmental perspective, and fungicides are not effective against the fungal spores that can persist in infected canola stubble from year to year. Constant use of fungicides can select for fungicide-resistant fungi, so improved methods of controlling fungal diseases are needed to protect plants in the vulnerable seedling stage and throughout the growing season. Biological control of blackleg and other fungal diseases may offer an environmentally sound method for plant disease control.

SUMMARY OF THE INVENTION

After considerable research and effort, a soil bacterium has been isolated from canola roots in a canola production plot near Sedgewick, Alberta Canada. The soil bacterium is a new strain of *Paenibacillus polymyxa* (formerly defined as *Bacillus polymyxa*) and has been called PKB1. A sample of the bacterium was deposited on May 18, 1998 with the American Type Culture Collection (ATCC), bearing ATCC Accession Number 202127. The soil bacterium produces an antibiotic after sporulation of the vegetative cells. The antibiotic is primarily spore associated. The antibiotic exhibits pesticidal activity against some bacteria and fungi. In particular, the *P. polymyxa* strain, PKB1 and the peptide antibiotic from PKB1 offer antifungal activity against *Leptosphaeria maculans*, the fungus that causes blackleg disease in canola, as well as other economically important disease-causing fungi including *Sclerotinia sclerotiorum, Marasmius oreades, Pythium pythioides, Rhizoctonia solani, Fusarium avenaceum* and *Alternaria brassicae*. When freeze dried or living cells of this *P. polymyxa* strain are applied to canola seeds they provide the plants germinating from the seed with protection against *L. maculans* in the stubble. Strain PKB1 of *P. polymyxa* can be used as a biocontrol agent against blackleg and other fungal diseases of canola.

The present invention relates to a novel strain of bacteria, referred to herein as PKB1, which has an inhibitory affect on fungi such as *L. maculans* and *S. sclerotiorum*. The present invention also relates to the antibiotic isolated from the bacterial strain PKB1, referred to herein as the PKB1 antibiotic, and the peptides of the antibiotic, referred to herein as the PKB1 peptides, which provide the inhibitory affect against fungi. The bacteria, antibiotic and peptides of the present invention can be used as pesticides and biocontrol agents against disease-causing fungi, for example, in crop plants.

One aspect of the invention pertains to an isolated *Paenibacillus polymyxa* strain PKB1 that acts as an inhibitory agent against *Leptosphaeria maculans* and other disease-causing fungi such as for example. *Sclerotinia sclerotiorum, Marasmius oreades, Pythium pythioides, Rhizoctonia solani, Fusarium avenaceum* and *Alternaria brassicae*. An "isolated" or "purified" bacterial strain is substantially free of materials from its natural environment including soil and biological matter including other bacterium or plant matter. The language "substantially free of materials from its natural environment" includes preparations or cultures of the bacterium in which the bacterium is separated from components of the environment in which it is naturally found. In one embodiment, the language "substantially free of materials from its natural environment" includes cultures having less than about 20% (by count) of non-PKB1 bacteria (also referred to herein as contaminating bacteria, contaminating bacteria does not include bioactive mutants or modified forms of strain PKB1), more preferably less than 10% (by count) of non-PKB1 bacteria and most preferably less than about 5% non-PKB1 bacteria.

The invention also pertains to bioactive mutants or modified forms of strain PKB1 which retain their inhibitory affect against *L. maculans*. As used herein, the term "bioactive mutants or modified forms of strain PKB1" is intended to include bacterium which have naturally mutated or by manipulations such as, for example, chemical or UV mutation or genetic modification or transformation been modified to have other characteristics such as, for example, antibiotic resistance.

As used herein, inhibition is a reduction in the growth or development of the fungi, for example, against control systems. Standard assays, such as those described herein, can be used to determine the ability of the strain or bioactive mutants or modified forms thereof to act against the fungi of interest. The standard assays can be conducted in vitro or in the field.

The strain or bioactive mutants or modified forms thereof can be in vegetative or spore state. They can be in culture, cell suspension, dried, dead or viable or in any other form such that they are capable of inhibiting L. maculans and preferably other disease-causing fungi.

Another aspect of the invention pertains to methods for detecting the presence of the bacterial strain of the present invention in a biological sample. In a preferred embodiment, the methods involve contacting a biological sample (e.g. a soil sample) with a compound or an agent capable of detecting PKB1 cells or nucleic acids such that the presence of PKB1 is detected in the biological sample. The compound or agent can be, for example, a labeled or labelable nucleic acid probe capable of hybridizing to PKB1 bacterium nucleic acids.

Another aspect of the invention pertains to an isolated antibiotic which is capable of inhibiting the development of *L. maculans*. In a preferred embodiment, the isolated antibiotic contains at least one of the spore-associated peptides of *Paenibacillus polymyxa* strain PKB1 or contains at least one peptide which is sufficiently homologous to the amino acid sequence of one of the spore-associated peptides of *Paenibacillus polymyxa* strain PKB1 and maintains the ability to inhibit the development of *L. maculans.*

In one embodiment, the antibiotic of the present invention comprises at least one peptide having an amino acid sequence of a spore-associated peptide of *Paenibacillus polymyxa* strain and that have inhibitory affect against *L. maculans*, or at least one peptide having an amino acid sequence of a spore-associated peptide of *Paenibacillus polymyxa* strain deposited with ATCC as Accession Number 202127 or, preferably, at least one peptide having an amino acid sequence of a spore-associated peptide of *Paenibacillus polymyxa* strain PKB1 having molecular weights of between 883 to 884 or between 896 to 897.

The invention also provides an isolated preparation of the PKB1 antibiotic. In preferred embodiments, the antibiotic preparation comprises at least one peptide having an amino acid sequence of a spore-associated peptide of *Paenibacillus polymyxa* strain, or at least one peptide having an amino acid sequence of a spore-associated peptide of *Paenibacillus polymyxa* strain deposited with ATCC as Accession Number 202127 or, preferably, at least one peptide having an amino acid sequence of a spore-associated peptide of *Paenibacillus polymyxa* strain PKB1 having molecular weights of between 883 to 884 or between 896 to 897 and has a inhibitory affect against *L. maculans.*

In one embodiment, the antibiotic includes two primary peptides. The peptides are each comprised of eight amino acids in a branched cyclic sequence and are nearly identical in form. One peptide has a molecular weight (MW) of about 897 to 898 and the second form has a molecular weight of about 883 to 884.

Another aspect of the invention pertains to an isolated peptide of the present invention or a fragment, or portion, e.g. a bioactive fragment or portion, thereof. In a preferred embodiment, the isolated peptide or bioactive fragment thereof can inhibit the development of *L. maculans*. In another preferred embodiment, the isolated peptide or bioactive fragment thereof is sufficiently homologous to the amino acid sequence of one of the spore-associated peptides of *Paenibacillus polymyxa* strain PKB1 and maintains the ability to inhibit the development of *L. maculans.*

In one embodiment, the peptide or bioactive fragment of the present invention comprise the amino acid sequence of a spore-associated peptide of *Paenibacillus polymyxa* strain, or the amino acid sequence of a spore-associated peptides of *Paenibacillus polymyxa* strain deposited with ATCC as Accession Number 202127 and preferably those spore-associated peptides of *Paenibacillus polymyxa* strain PKB1 having molecular weights of between 883 to 884 and/or between 896 to 897 and have inhibitory affect against *L. maculans*. In one preferred embodiment, the peptide or bioactive fragment of the present invention comprises one valine, one alanine, one threonine, two aspartic acids, one proline, one acetyl-modified leucine and one glutamic acid and being capable of inhibiting *L. maculans*. In another preferred embodiment, the peptide or bioactive fragment of the present invention comprises the amino acid sequence according to FIG. 6B.

The invention also provides an isolated preparation of the peptide according to the present invention. In preferred embodiments, the peptide of the preparation comprise the amino acid sequence of a spore-associated peptide of *Paenibacillus polymyxa* strain, or the amino acid sequence of a spore-associated peptides of *Paenibacillus polymyxa* strain deposited with ATCC as Accession Number 202127 and preferably those spore-associated peptides of *Paenibacillus polymyxa* strain PKB1 having molecular weights of between 883 to 884 and/or between 896 to 897 and have inhibitory affect against *L. maculans*. In one preferred embodiment, the peptide or bioactive fragment of the present invention comprises one valine, one alanine, one threonine, two aspartic acids, one proline, one acetyl-modified leucine and one glutamic acid and being capable of inhibiting *L. maculans*. In another preferred embodiment, the peptide or bioactive fragment of the present invention comprises the amino acid sequence according to FIG. 6B. In yet another embodiment, the peptide is at least about 50–60%, preferably at least about 65–70%, more preferably at least about 75–80%, and even more preferably at least 85, 90, 95% or more homologous to the entire amino acid sequence of FIG. 6B. In other embodiments, the isolated peptide comprises an amino acid sequence which is at least about 60–70% or more homologous to the amino acid sequence of FIG. 6B and has an one or more of the following activities: 1) it can inhibit development of *L. maculans* and 2) it can inhibit development of *S. sclerotiorum.*

The peptide or a bioactive fragment thereof, as defined above, can be operatively linked to another peptide to form a fusion protein. In addition, the PKB1 peptide or a bioactive fragment thereof can be incorporated into a pesticide composition comprising the peptide and an acceptable carrier or enhancer.

The *P. polymyxa* antibiotic producing strain PKB1 according to the present invention offers promise for use as a biocontrol agent because it is active against many fungal diseases. Biocontrol agents are relatively inexpensive to mass produce because they are grown in large volume fermenters and require little or no downstream processing other than, in some embodiments, drying. Unlike the situation with chemical fungicides, once a crop has been treated with a biocontrol agent, it may not need to be treated again for several years because the biocontrol agent is a live organism and can sustain itself in the soil environment. In this regard, the bacterium of the present invention is a preferred organism for use as a biocontrol agent because it forms dormant spores which are extremely resistant to heat, drying, chemical treatment, radiation and ultraviolet light exposure. This makes it possible to store dried cells of

*Paenibacillus polymyxa.* PKB1 for long periods with little loss of viability. The same-spore forming ability occurs in the soil, making it possible for the introduced *P. polymyxa* strain to survive long periods of dryness or harsh conditions.

DETAILED DESCRIPTION OF THE DRAWINGS

Figure 3:
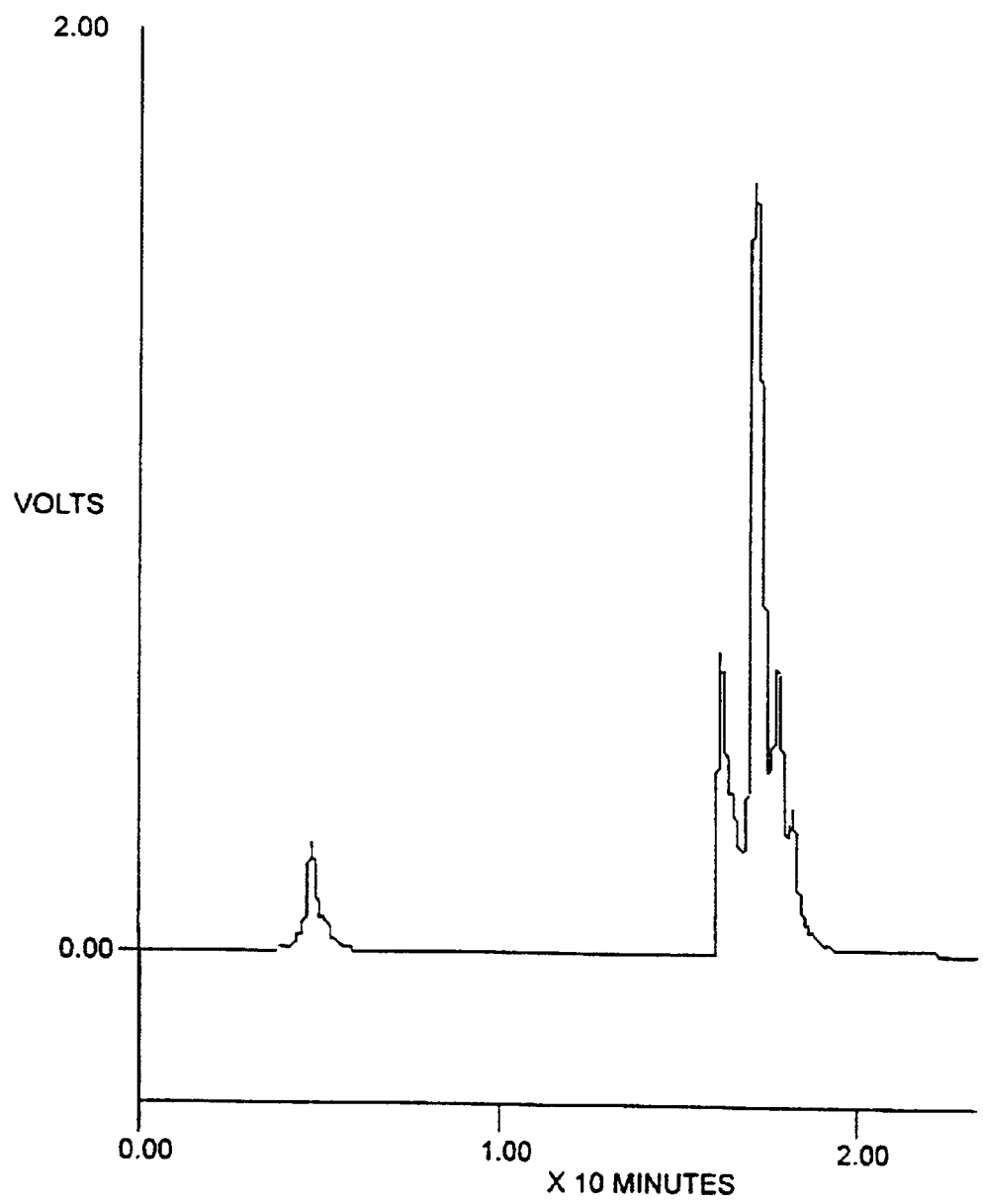

FIG. 3 is a reverse phase high performance liquid chromatography trace of the antifungal antibiotic. The active fraction is found at peaks 17.0 and 17.7. A linear mobile phase gradient was used of (A) acetonitrile, 60% B to 100% B. The flow rate was 1.0 ml/min, detection at 214 nm, fractions collected every 60 seconds.

Figures 4, 5:
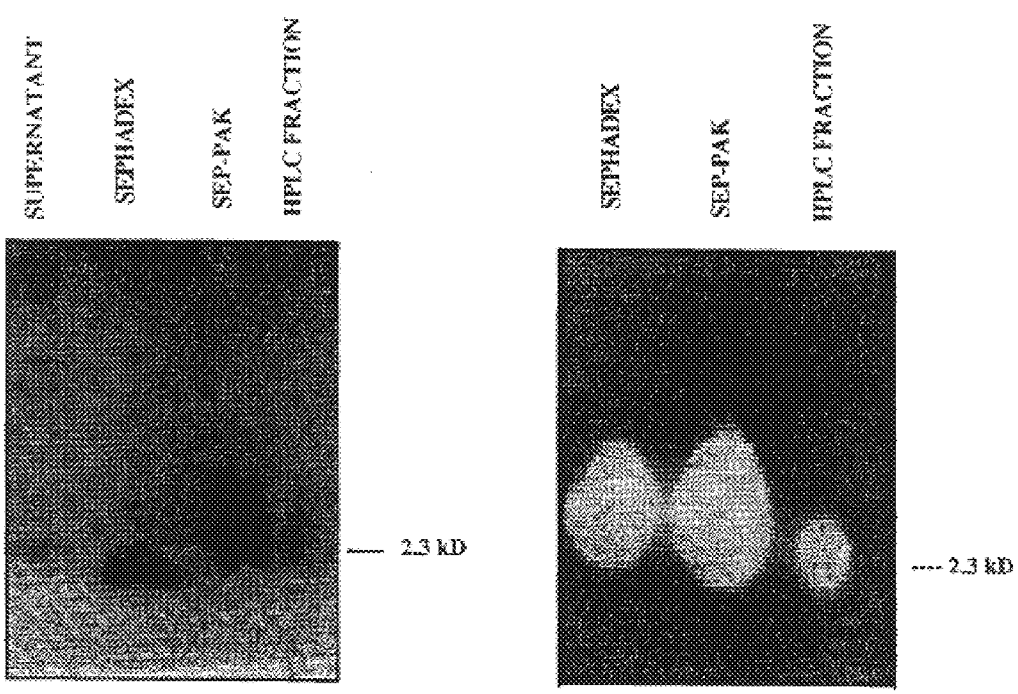

FIG. 4 is a photo of the 16.5% acrylamide SDS-PAGE. Peptide was stained with coomassie blue. Bands seen correspond to the molecular weight standard of 2.3 kDa.

FIG. 5 is a bioautograph of the 16.5% acrylamide SDS-PAGE using *L. maculans* as the indicator organism. Zones of inhibition that correspond to the bands in the SDS-PAGE of FIG. 4 can be seen.

Figure 6A:
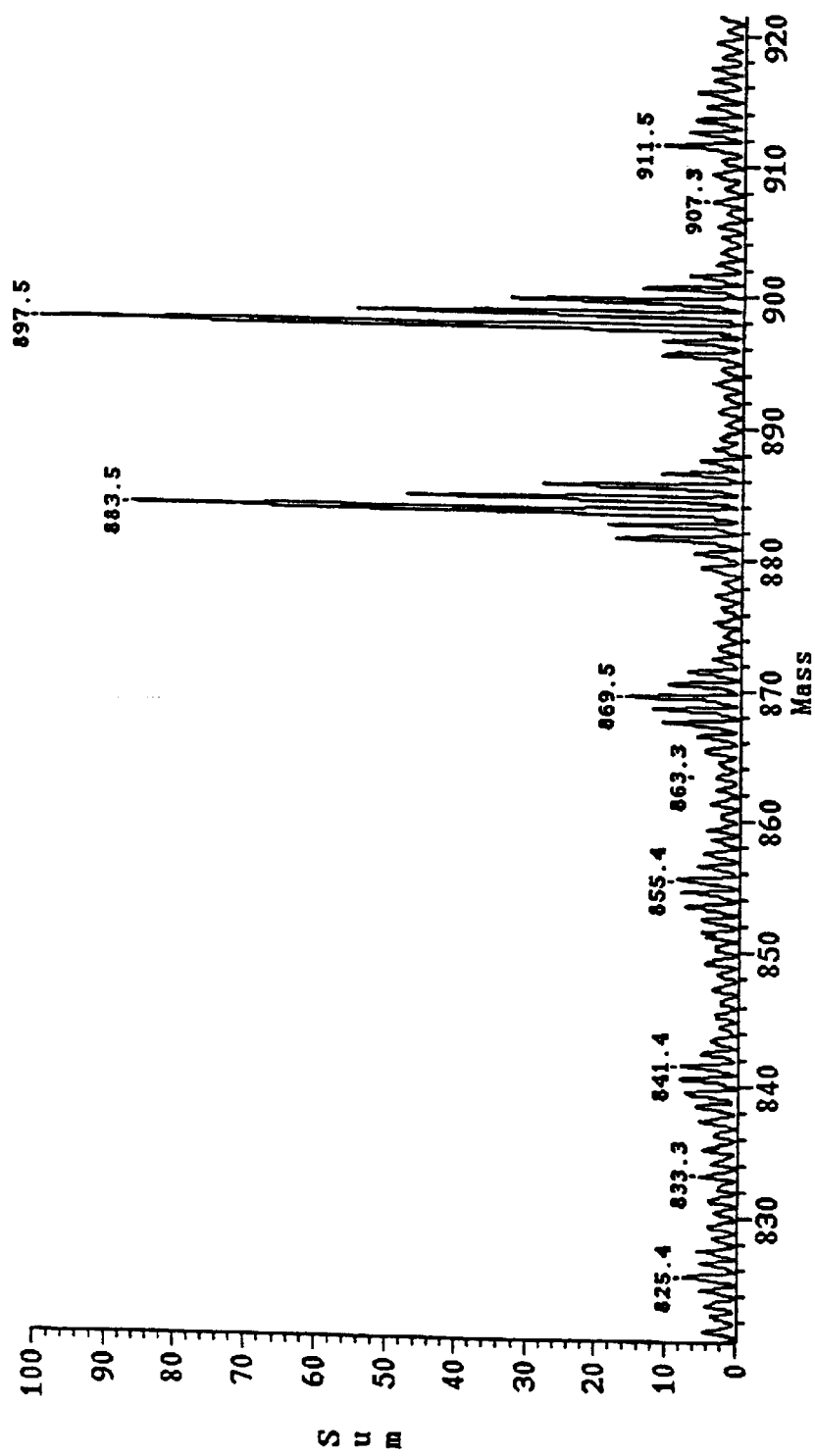

FIG. 6A is a chart of the fast atom bombardment mass spectrum of pure antifungal antibiotic. Two components are seen to determine an active antibiotic, one at 883.5 molecular weight and the other at 897.5 molecular weight. The sample was ionized using a glycerine/thioglycerol matrix.

Figure 6B:
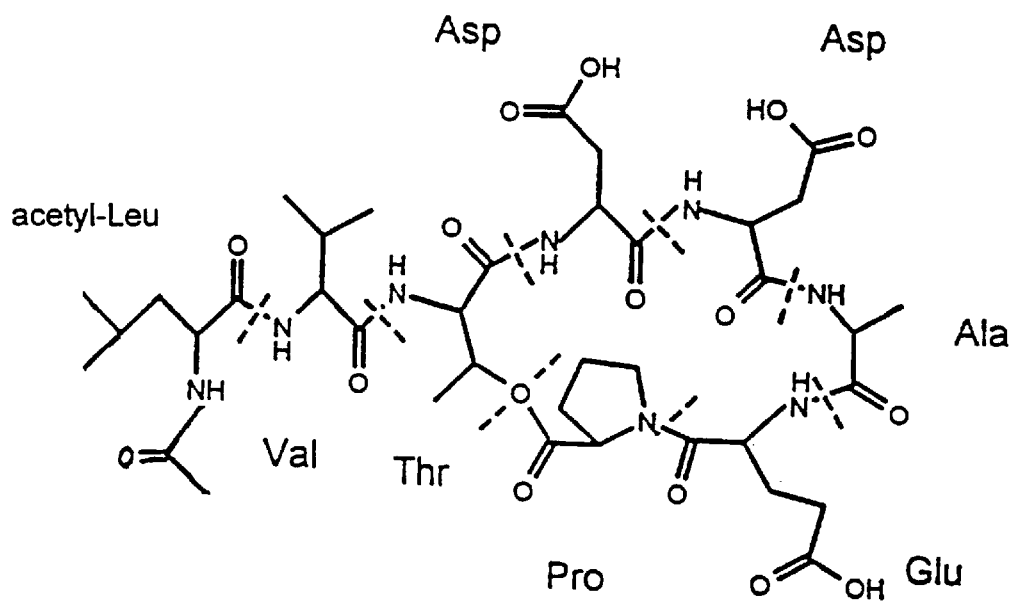

FIG. 6B is a proposed structural formula for antibiotic peptide 883.5 MW.

Figure 7:
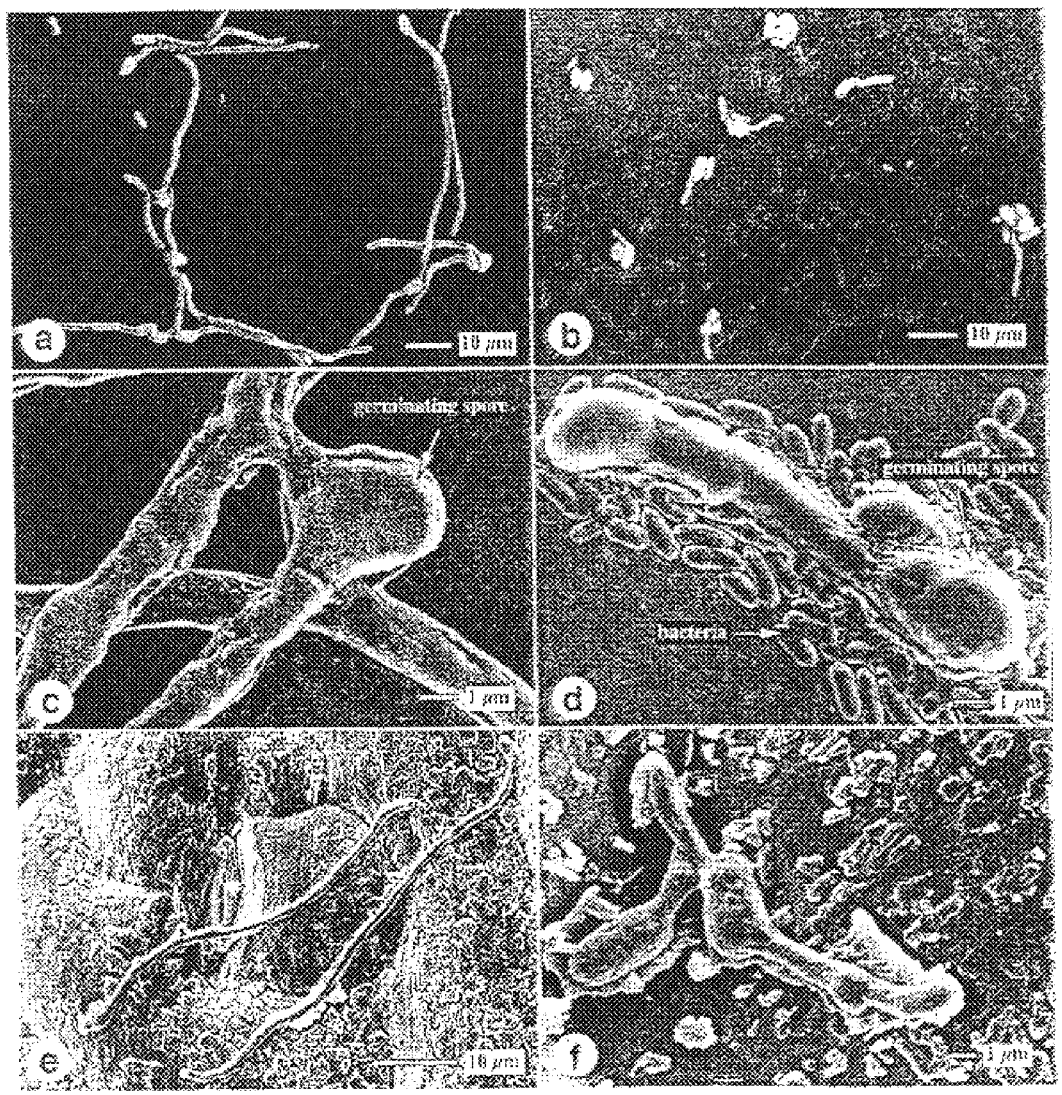

FIG. 7 shows scanning electron micrographs of germination of pycnidiospores of *Leptosphaeria maculans* (a) without bacterial treatment and (b) treated with *Paenibacillus polymyxa* PKB1 on a cellophane membrane after two days incubation at room temperature; (c) without bacterial treatment and (d) treated with *Paenibacillus polymyxa* PKB1 on cellophane membrane after three days incubation at room temperature, (e) without bacterial treatment and (f) treated with bacterium on the canola leaf surface after three days incubation in a greenhouse.

Figure 8:
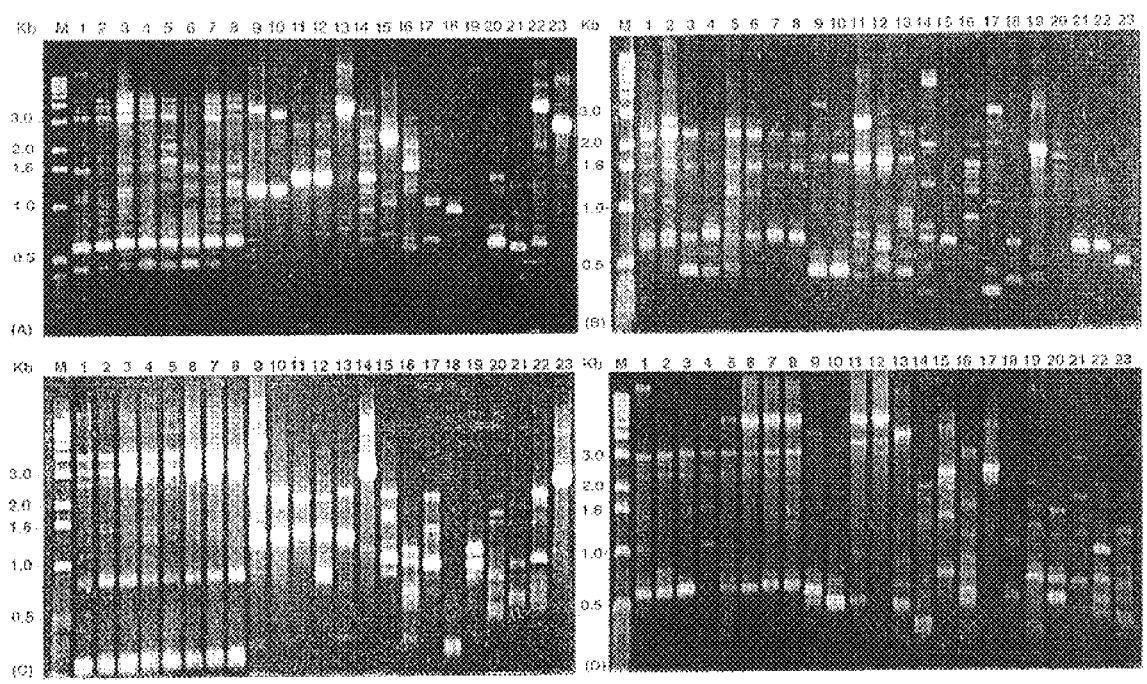

FIG. 8 shows DNA patterns on 23 bacterial strains of *Paenibacillus polymyxa* and Bacillus spp. amplified with primers OPA07 (A), OPA08 (B), OPA13 (C), and OPA14 (D).

Figure 9:
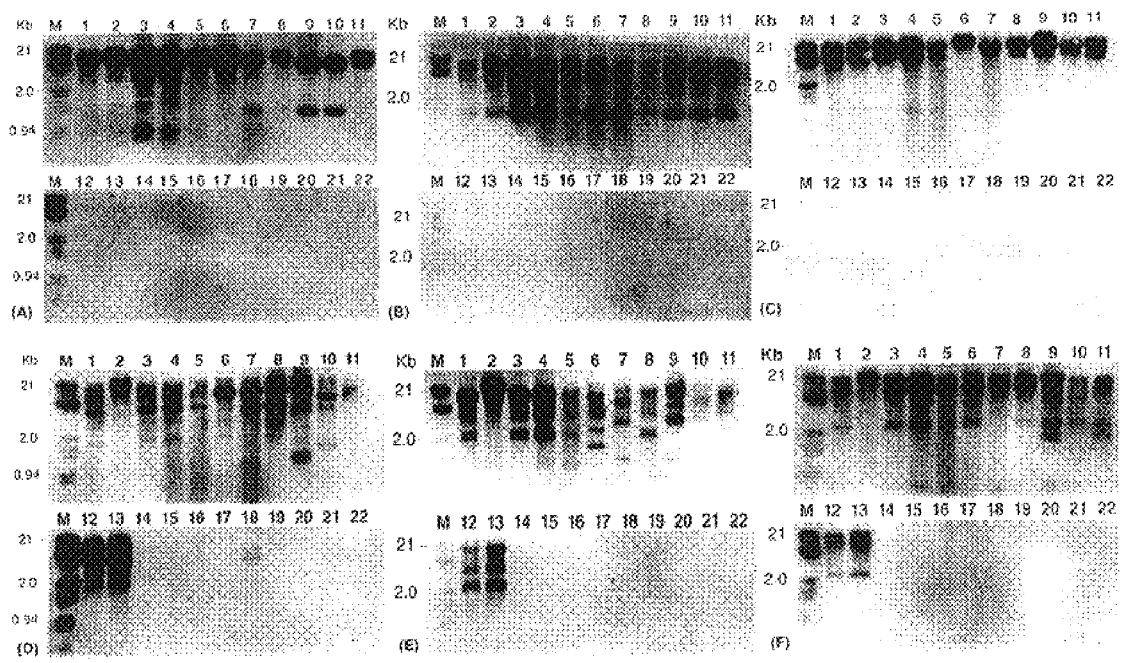

FIG. 9 shows autoradiographs of Southern blot of 22 bacterial strains of *Paenibacillus polymyxa* and Bacillus spp. DNA digested with HindIII (A,B), PstI (C) and EcoRI (D,E, and F), and hybridized with P1–7 (A,C, and D), P1–8 (E), P1–14 (B,F).

Figure 10:
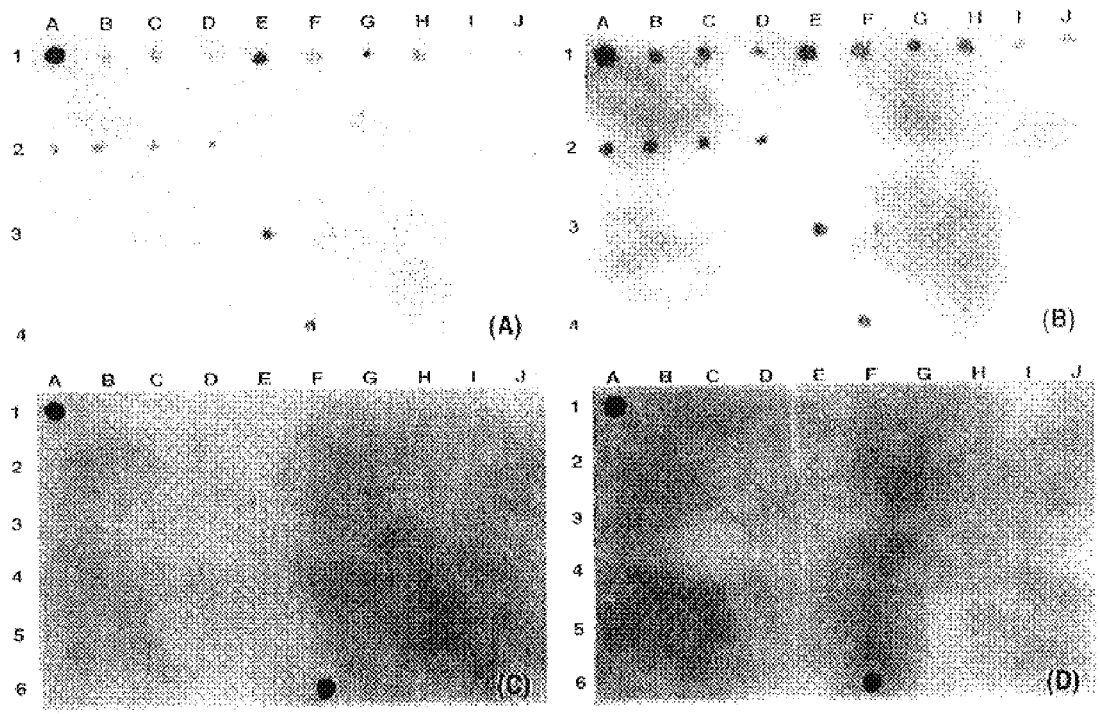

FIG. 10 shows dot-blotting of 23 bacterial strains of *Paenibacillus polymyxa* and Bacillus spp. with probes 1–7 (A) and 1–8 (B), and 52 unknown bacteria strains from compost and canola stubble probed with P1–7 (C) and P1–8 (D).

FIG. 11 shows the DNA sequence of probe P1–8 (SEQ ID NO:6).

Figure 12:
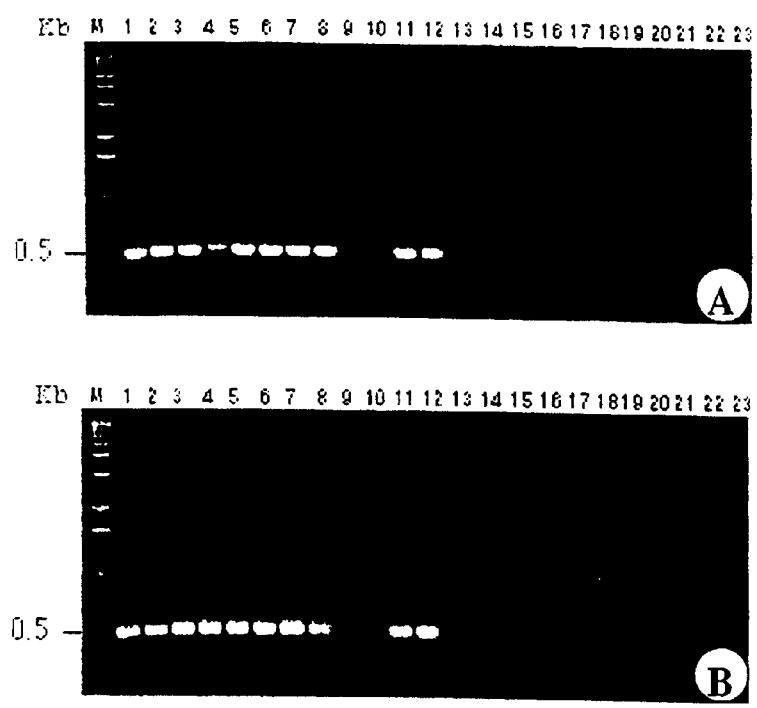

FIG. 12 shows the PCR products of 23 bacterial strains of *Paenibacillus polymyxa* and Bacillus spp. amplified with primers (A) J1 and JY1, and (B) J1 and JY2.

Figure 13:
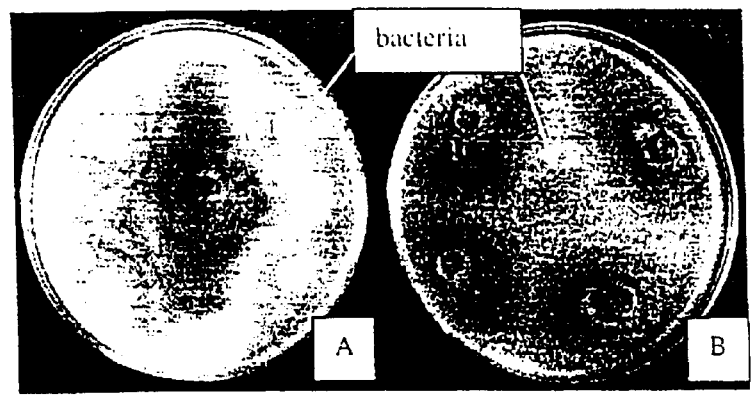

FIG. 13 shows photos of (A) a plate showing the inhibitory effect of strain 97-003 inoculated compost and (B) a control plate.

DETAILED DESCRIPTION OF THE INVENTION

The present invention relates to a novel strain of bacteria, referred to herein as PKB1, which has an inhibitory affect on fungi such as *L. maculans* and *S. sclerotiorum*. The present invention also relates to the antibiotic isolated from the bacterial strain PKB1, referred to herein as the PKB1 antibiotic, and the peptides of the antibiotic, referred to herein as the PKB1 peptides, which provide the inhibitory affect against fungi. The bacteria, antibiotic and peptides of the present invention can be used as pesticides and biocontrol agents against disease-causing fungi, for example, in crop plants.

The bacterial strain PKB1, which is a *Paenibacillus polymyxa*, has been deposited with the American Type Culture Collection (ATCC), Manassas, Va., on May 18, 1998 and assigned Accession Number 202127. The antibiotic extracted from the bacteria is a peptide antibiotic including primarily two cyclic peptides of eight amino acids each. The sequence of one of the peptides is shown in FIG. 6B. The peptides or bioactive fragments thereof according to the invention have inhibitory affect against disease-causing fungi.

Various aspects of the present invention are described in further detail in the following subsections.

I. Isolated Bacterial Strain

One aspect of the invention pertains to an isolated *Paenibacillus polymyxa* strain PKB1 that acts as an inhibitory agent against *Leptosphaeria maculans* and other disease-causing fungi such as for example *Sclerotinia sclerotiorum, Marasmius oreades, Pythium pythioides Rhizoctonia solani, Fusarium avenaceum* and *Alternaria brassicae*. An "isolated" or "purified" bacterial strain is substantially free of materials from its natural environment including soil and biological matter including other bacterium or plant matter. The language "substantially free of materials from its natural environment" includes preparations or cultures of the bacterium in which the bacterium is separated from components of the environment in which it is naturally found. In one embodiment, the language "substantially free of materials from its natural environment" includes cultures having less than about 20% (by count) of non-PKB1 bacteria (also referred to herein as contaminating bacteria, contaminating bacteria does not include bioactive mutants or modified forms of strain PKB1), more preferably less than 10% (by count) of non-PKB1 bacteria and most preferably less than about 5% non-PKB1 bacteria.

The invention also pertains to bioactive mutants or modified forms of strain PKB1 which retain their inhibitory affect against *L. maculans*. As used herein, the term "bioactive mutants or modified forms of strain PKB1" is intended to include bacterium which have naturally mutated or by manipulations such as, for example, chemical or UV mutation or genetic modification or transformation been modified to have other characteristics such as, for example, antibiotic resistance.

As used herein, inhibition is a reduction in the growth or development of the fungi, for example, against control systems. Standard assays, such as those described herein, can be used to determine the ability of the strain or bioactive mutants or modified forms thereof to act against the fungi of interest. The standard assays can be conducted in vitro or in the field.

The strain or bioactive mutants or modified forms thereof can be in vegetative or spore state. They can be in culture, dried, dead or viable or in any other form such that they are capable of inhibiting *L. maculans* and preferably other disease-causing fungi.

II. Isolated PKB1 Antibiotic and Peptides

Another aspect of the invention pertains to isolated PKB1 antibiotic and peptides or bioactive fragments or portions thereof. An "isolated" or "purified" antibiotic or peptide or bioactive fragments thereof is substantially free of cellular material when produced by extraction from a bacterial system, or chemical precursors or other chemicals when chemically synthesized. The language "substantially free of cellular material" includes preparations of PKB1 peptide in which the antibiotic or peptide is separated from cellular components of the bacteria, or in particular, the bacterial spores on which it is produced. In one embodiment, the language "substantially free of cellular material" includes preparations having less than about 30% (by dry weight) of non-PKB1 peptides or protein (also referred to herein as contaminating protein), more preferably less than 20% (by dry weight) of non-PKB1 peptides or protein, still more preferably less than about 10% (by dry weight) of non-PKB1 peptides or protein and most preferably less than about 5% (by dry weight) of non-PKB1 peptides or protein. The language "substantially free of chemical precursors or other chemicals" includes preparations of PKB1 peptides in which the peptides are separated from chemical precursors or other chemicals which are involved in the synthesis of the peptides. In one embodiment, the language "substantially free of chemical precursors or other chemicals" includes preparations having less than about 30% (by dry weight) of chemical precursors or non-PKB1 chemicals, more preferably less than 20% (by dry weight) of chemical precursors or non-PKB1 chemicals, still more preferably less than about 10% (by dry weight) of chemical precursors or non-PKB1 chemicals and most preferably less than about 5% (by dry weight) of chemical precursors or non-PKB1 chemicals. In preferred embodiments, isolated PKB1 antibiotic or peptides or bioactive fragments thereof are free of contaminating proteins from the same bacteria from which the antibiotic or peptides are derived. Typically, such antibiotic and peptides are produced by extraction from the bacteria which produces them.

Isolated PKB1 antibiotic and peptides or bioactive fragments or portions thereof according to the present invention act against *L. maculans*. In one embodiment, the antibiotic of the present invention comprises at least one peptide having an amino acid sequence of a spore-associated peptide of *Paenibacillus polymyxa* strain and that have inhibitory affect against *L. maculans*, or at least one peptide having an amino acid sequence of a spore-associated peptide of *Paenibacillus polymyxa* strain deposited with ATCC as Accession Number 202127 or, preferably, at least one peptide having an amino acid sequence of a spore-associated peptide of *Paenibacillus polymyxa* strain PKB1 having molecular weights of between 88, to 884 or between 896 to 897.

The invention also provides an isolated preparation of the PKB1 antibiotic. In preferred embodiments, the antibiotic preparation comprises at least one peptide having an amino acid sequence of a spore-associated peptide of *Paenibacillus polymyxa* strain, or at least one peptide having an amino acid sequence of a spore-associated peptide of *Paenibacillus polymyxa* strain deposited with ATCC as Accession Number 202127 or, preferably at least one peptide having an amino acid sequence of a spore-associated peptide of *Paenibacillus polymyxa* strain PKB1 having molecular weights of between 883 to 884 or between 896 to 897 and has a inhibitory affect against *L. maculans*.

In one embodiment, the antibiotic includes two primary peptides. The peptides are each comprised of eight amino acids in a branched cyclic sequence and are nearly identical in form. One peptide has a molecular weight (MW) of about 897 to 898 and the second form has a molecular weight of about 883 to 884.

Another aspect of the invention pertains to an isolated peptide of the present invention or a fragment, or portion, e.g. a bioactive fragment or portion, thereof. In a preferred embodiment, the isolated peptide or bioactive fragment thereof can inhibit the development of *L. maculans*. In another preferred embodiment, the isolated peptide or bioactive fragment thereof is sufficiently homologous to the amino acid sequence of one of the spore-associated peptides of *Paenibacillus polymyxa* strain PKB1 and maintains the ability to inhibit the development of *L. maculans*.

In one embodiment, the peptide or bioactive fragment of the present invention comprise the amino acid sequence of a spore-associated peptide of *Paenibacillus polymyxa* strain, or the amino acid sequence of a spore-associated peptides of *Paenibacillus polymyxa* strain deposited with ATCC as Accession Number 202127 and preferably those spore-associated peptides of *Paenibacillus polymyxa* strain PKB1 having molecular weights of between 883 to 884 and/or between 896 to 897 and have inhibitory affect against *L. maculans*. In one preferred embodiment, the peptide or bioactive fragment of the present invention comprises one valine, one alanine, one threonine, two aspartic acids, one proline, one acetyl-modified leucine and one glutamic acid and being capable of inhibiting *L. maculans*. In another preferred embodiment, the peptide or bioactive fragment of the present invention comprises the amino acid sequence according to FIG. 6B.

The invention also provides an isolated preparation of the peptide according to the present invention. In preferred embodiments, the peptide of the preparation comprise the amino acid sequence of a spore-associated peptide of *Paenibacillus polymyxa* strain, or the amino acid sequence of a spore-associated peptides of *Paenibacillus polymyxa* strain deposited with ATCC as Accession Number 202127 and preferably those spore-associated peptides of *Paenibacillus polymyxa* strain PKB1 having molecular weights of between 883 to 884 and/or between 896 to 897 and have inhibitory affect against *L. maculans*. In one preferred embodiment the peptide or bioactive fragment of the present invention comprises one valine, one alanine, one threonine, two aspartic acids, one proline one acetyl-modified leucine and one glutamic acid and being capable of inhibiting *L. maculans*. In another preferred embodiment, the peptide or bioactive fragment of the present invention comprises the amino acid sequence according to FIG. 6B. In yet another embodiment, the peptide is at least about 65–70%, more preferably at least about 75–80% and even more preferably at least 85, 90, 95% or more homologous to the entire amino acid sequence of FIG. 6B. In other embodiments, the isolated peptide comprises an amino acid sequence which is at least about 60–70% or more homologous to the amino acid sequence of FIG. 6B and has an one or more of the following activities: 1) it can inhibit development of *L. maculans* and 2) it can inhibit development of *S. sclerotiorum*.

As used herein, the language "sufficiently homologous" refers to the peptides or fragments thereof which have amino acid sequences which include a minimum number of identical or equivalent (e.g. an amino acid residue which has a similar side chain as an amino acid residue in the peptides of the present invention) amino acid residues to an amino acid sequence of a peptide of the PKB1 antibiotic while retaining its inhibitory affect against *L. maculans*. To determine the percent homology of two amino acid sequences, the sequences are aligned for optimal comparison purposes (e.g. gaps can be introduced in the sequence of one sequence for optimal alignment with he other sequence). The amino acid residues at corresponding amino acid positions are then compared. When a position in one sequence is occupied by the same amino acid residue as the corresponding position in the other sequence, then the molecules are homologous at that position. The percent homology between the two sequences is a function of the number of identical positions shared by the sequences (i.e. % homology=# of identical positions/total# of positions×100).

Bioactive fragments or portions of the PKB1 peptides include amino acid sequences derived from the amino acid sequence of the (insert) and exhibit the inhibitory affect against *L. maculans*.

PKB1 antibiotic and peptides are preferably produced by extraction from bacterial strain PKB1. The extraction procedure includes treating the spores of the bacterium with a solvent of medium polarity of, for example, between 5.5 to 7.5 using the nine point scale of N. Godfrey (Solvent selection via miscibility number, Chemtech pp 359–363, 1972). The extraction is preferably carried out with methanol or acetic acid. Alternately, the peptides of the present invention can be produced recombinantly or by chemical synthesis.

The invention also provides PKB1 chimeric or fusion proteins. As used herein "chimeric" or "fusion" proteins comprise a PKB1 peptide operatively linked to a non-PKB1 peptide or protein. A PKB1 peptide is a peptide or bioactive fragment or portion thereof as defined hereinbefore, whereas a "non-PKB1 peptide or protein refers to a peptide or protein having an amino acid sequence corresponding to a protein which is not substantially homologous to any one of the PKB1 peptides, e.g. a protein that is different from the PKB1 peptides and which is derived from the same or a different organism. Within the fusion protein, the term "operatively linked" is intended to indicate that the PKB1 peptide and the non-PKB1 peptide or protein are fused in-frame to each other. The non-PKB1 peptide or protein can be fused to the PKB1 peptide in any suitable way provided that it does not eliminate the antibiotic function of the peptide. Such fusion or chimeric proteins can be selected to enhance, for example, delivery, handling, purification or effect of the PKB1 peptide from which it is formed. Fusion or chimeric proteins can be produced by any desired means.

III. Uses and Methods of the Invention

The bacterial strain, antibiotic and peptides of the present invention can be used as a pesticide against some bacteria and fungi.

The bacterial strain or bioactive mutants or modified forms thereof of the present invention can be used as a pesticide and, in particular, a biocontrol agent against some bacteria and fungi including *Leptosphaeria maculans, Sclerotinia sclerotiorum, Pythium pythioides, Marasmius oreades, Rhizoctonia solani, Fusarium avenaceum* and *Alternaria brassicae*. As would be appreciated, for biocontrol of disease-causing fungi, the bacteria is preferably applied to a crop to act against the fungal diseases therein. The bacteria can be applied in any suitable way including in a live or dead, vegetative state, in a spore state. The bacteria can be dried or hydrated. In a preferred embodiment, the bacteria is applied in a viable form which permits it to sustain itself in the soil to provide a biocontrol effect over a long period of time. Bioassay methods can be used to determine the presence of the bacteria in the environment.

In accordance with another aspect of the invention, PKB1 antibiotic or PKB1 peptides or bioactive fragments or portions thereof can be used as a pesticide against some bacteria and fungi including *Leptosphaeria maculans, Sclerotinia sclerotiorum, Marasmius oreades, Pythium pythioides, Rhizoctonia solani, Fusarium avenaceum* and *Alternaria brassicae*. The PKB1 antibiotic or PKB1 peptides or bioactive fragments or portions thereof can be applied to a crop at any desired stage of crop growth to act against the fungal diseases therein. Fusion proteins of the PKB1 peptides can also be used as pesticides.

The bacterial strain, antibiotic and peptides of the present invention can be applied as a pesticide in any desired way. In one embodiment, the bacterial strain, antibiotic and peptides are applied in a carrier to facilitate application and to reduce crop maintenance time. In particular, in one embodiment, the PKB1 bacterial strain is cultured in compost and applied to a crop with the compost.

The following examples further demonstrate several embodiments of this invention. While the examples illustrate the invention, they are not intended to limit it.

EXAMPLES

I. Characterization of the Isolated Bacterium

Upon discovery of the bacterium it was necessary to characterize it. As a first step, biochemical tests were used to analyze the bacterium. These tests characterized the bacterium as *Bacillus polymyxa*. Since the time of the early work, the genus Bacillus has undergone a redefinition based on 16S rRNA sequence homology. It was desirable to characterize this isolate on the basis of molecular tests as well. Using 16S rRNA homology the isolate was determined to be *Paenibacillus polymyxa*.

I.i Characterization of the Bacillus Species PKB1

Biochemical tests designed to determine the identity of unknown bacteria was used to analyze the bacterium. These tests can specifically differentiate between different species of the genus Paenibacillus. Two different Bacillus spp. were obtained from the American Type Culture Collection (ATCC) and used as standards in these tests; *B. macerans* ATCC accession no. 8244 and *B. circulans* ATCC accession no. 4513. *B. polymyxa* NCIB 4868 was used as the *B. polymyxa* type culture.

Preliminary taxonomic studies on strain PKB1 indicated that the organism was most closely related to *Bacillus polymyxa*. Biochemical tests confirmed the isolate as *B. polymyxa* after comparison of the test results with the test results of three Bacillus type cultures. *B. polymyxa* strain PKB1 differs from the *B. polymyxa* type culture in several ways. The environmental isolate grows more vigorously on most culture media and produces more extracellular polysaccharides. As well, the type culture *B. polymyxa* is not able to inhibit the growth of *L. maculans*.

Fatty acid methyl ester analysis (FAME) was performed on the bacterial isolate according to the method of Stockman et al (Stockman, L., Roberts, G. D. and Smith, D. H., "Identification of mycobacteria by cell wall composition with the HP microbial identification system" Abstracts of the 87th meeting of American Society of Microbiology, 1987).

Comparison of fatty acid profiles of bacterial cell walls is a common method to determine the relatedness of bacterial strains. The data from the FAME is entered into a cluster program such as the dendrogram program that produces unweighted pair matchings and form a diagram such as a tree that displays the relatedness of the organisms tested, measured in Euclidean distances. A distance of 25 or less means the organisms are related at the genus level and 10 or less means they are related at the species level.

Figure 1A:
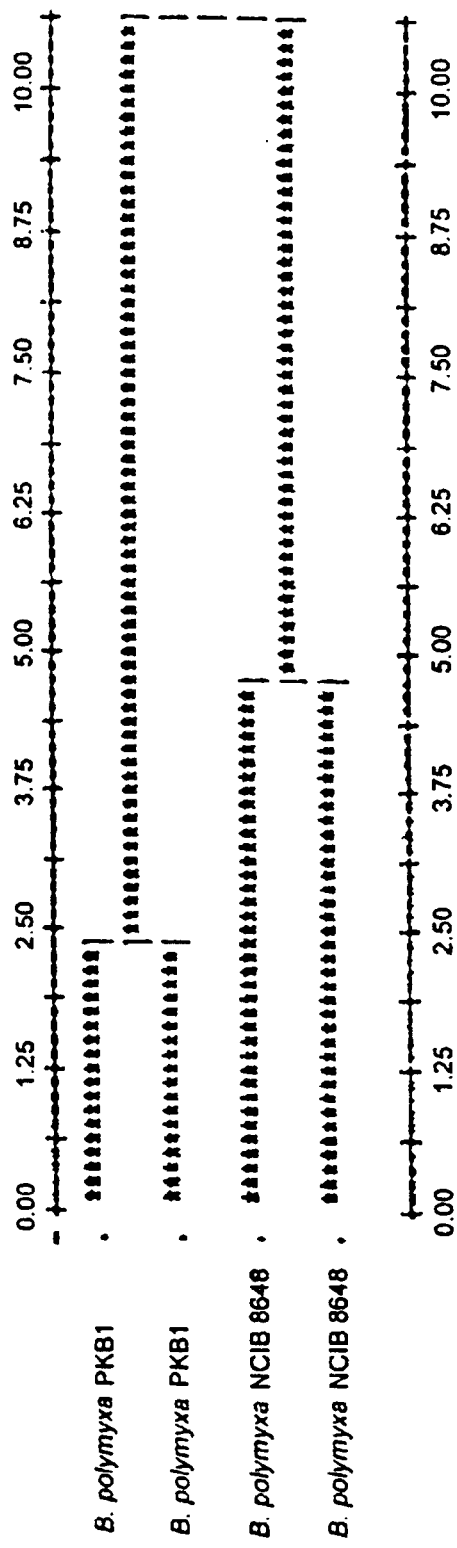
FIG. 1A is a Euclidian chart from the fatty acid methyl ester analysis (FAME analysis) of (A) the PKB1 strain and (B) *B. polymyxa* NCIB 8648.

Using FAME analysis (FIG. 1A), the isolate was within 3 Euclidean distances of the type culture. Therefore, the PKB1 is the same genus and species as the type culture B. polymyxa.

I.ii Characterization of the Paenibacillus Species PKB1 Using 16S rRNA

I.ii.a. Primer Design

Two primers were designed for generating a PCR fragment encompassing most of the 16S rRNA sequence present in P. polymyxa PKB1. These primers were also used for the initial portion of the sequencing reaction. The forward primer, 8F, encompassed the forward amplification primer sequence 16F27 from Hauben et al. (Hauben L., L. Vauterin. J. Swings and E. R. B. Moore. 1997. Comparison of 16S ribosomal DNA sequences of all Xanthomonas species. International Journal of Systematic Bacteriology. 47, pp 328–335) and a sequence that contained sites for the restriction enzymes SacI, EcoRI and Xba. The reverse primer sequence (1403R) encompassed the reverse amplification primer sequence 1387R from Marchesi et al. (Marchesi J. R., Sato T., Weightman A. J., Martin T. A., Fry J. C., Hiom S. J., and Wade W. G. 1998. Design and evaluation of useful bacterium specific PCR primers that amplify genes coding for bacterial 16S rRNA. Applied and Environmental Microbiology. 64(2):795–799) and the reverse of the restriction enzyme site sequence. The restriction enzyme sites were added to the PCR primers so that if it were necessary to clone the PCR fragment into a plasmid for further genetic analyses, there would be an easy means to prepare it. The primer sequences were compared with those for the E. coli 16S rRNA sequence (Carbon P., Ehresmann C., Ehresmann B. and Ebel J-P. 1979. The complete nucleotide sequence of the ribosomal 16S RNA from Escherichia coli. European Journal of Biochemistry. 100:399–410.); the primers described above extend from nucleotides 8 to 27 in a forward direction and from nucleotides 1403 to 1386 as a reverse complement to the reported sequence, which is a total of 1541 nucleotides in length.

The amplification primers described above were used as sequencing primers to obtain the end portions of the P. polymyxa PKB1 16S rRNA sequence. Other sequencing primers were designed based on a series of 10 primers described by Hauben et al. (1997). Modifications to the suggested sequences were made based on the sequence for P. polymyxa which was obtained using the amplification primers. A summary of these primers is shown in Table 0A.

TABLE 0A

Amplification and sequencing primers used to determine the 16S rRNA sequence of P. polymyxa PKB1. Primers were based on similar sequences reported by Hauben et al. (1997).

| primer name | primer sequence | application |
|---|---|---|
| 8F | 5'GAGCTCTAGAATTCAGAGTTTGATCATGGCTCAG3' | amplification |
| 704F | 5'TGTGTAGCGGTGAAATGCGTAGA3' | sequencing |
| 1176F | 5'AGGAAGGGGGGGAGGAGGT3' | sequencing |
| 358R | 5'CCCACTGGTGCCTCCCGTA3' | sequencing |
| 1106R | 5'CGCCCTTTTCGGGACTTAACCC3' | sequencing |
| 1403R | 5'TCGAGCTCTAGAATTCGGGCGGTGTGTACAAGGC3' | amplification |

In the attached Sequence Listing primer 8F is listed as SEQ ID NO:1, primer 704F is listed as SEQ ID NO:2, primer 1176F is listed as SEQ ID NO:3, primer 358R is listed as SEQ ID NO:4, primer 1106R is listed as SEQ ID NO:5 and primer 1403R is listed as SEQ ID NO:7.

Generation of 16S rRNA PCR fragment from P. polymyxa PKB1 genomic DNA: A PCR protocol that produced the maximum amount of 16S rRNA from P. polymyxa PKB1 genomic DNA, using the primers 8F and 1403R (Table 0A), was developed. This protocol was used to generate DNA fragments for sequencing in order to determine the 16S rRNA sequence. The concentration of genomic and primer DNA was determined spectrophotometrically using the A260 of a DNA solution in water. PCR reactions were carried out in an MJ Research Minicycler. The temperature program was designed based on those of Hauben et al. (1997) and Marchesi et al. (1998), with modifications developed experimentally to suit P. polymyxa gene amplification, and is shown in Table 0B.

TABLE 0B

Temperature program for amplification of the 16S rRNA fragments of P. polymyxa by PCR.

| step | protocol |
|---|---|
| 1 | 5 min 94° C. |
| 2 | 30 s 94° C. denaturation of DNA primers and template |
| 3 | 30 s 55° C. annealing of DNA primers and templates |
| 4 | 1.5 min 72° C. extension of new DNA strands |
| 5 | repeat steps 2 through 4, 29 times |
| 6 | 5 min 72° C. extension of new DNA strands |
| 7 | 4° C. stop PCR reaction and refrigerate DNA product |
| 8 | end |

PCR generation of the 8F-1403R PCR fragment for sequencing was carried out in a set of 16 identical reaction tubes. Reactions contained: 1.2 mL 25 ng/mL genomic DNA, 0.67 mL each of 30 pmol/mL primer 8F and 30 pmol/mL primer 1403R, 0.4 mL 25 mM dNTP mix (25 mM each of dATP, dCTP, dGTP and dTTP, Boeringher Mannheim), 5 ml 10×PCR buffer, 0.75 mL 0.1 M MgCl2, 28.25 mL sterile deionized, distilled water and 1 mL 5 units/mL taq DNA polymerase (synthesized by A. Hashimoto and M. A. Pickard. Dept. of Biological Sciences, University of Alberta, Edmonton. AB). PCR buffer (10×) contained 0.5 g KCl, 8.48 g tris(hydroxymethyl) aminomethane hydrochloride (Tris-HCl, pH 8.8) 1 mL 1% Triton X-100 per 100 mL in deionized, distilled water. After preparation, a small amount of sterile mineral was put in each tube. The taq DNA polymerase was not added to the reaction mix until the program had run for approximately 2 min; at this time the PCR tubes were opened, enzyme was added beneath the mineral oil layer, and the program was allowed to continue. This 'hot start' procedure was used in order to decrease possible nonspecific product formation.

Purification of fragment: The approximately 1400 base pair (bp) DNA fragment produced by PCR amplification of the *P. polymyxa* PKB1 16S rRNA gene was purified for sequencing. After PCR, the aqueous portion of each reaction tube was transferred to a sterile 1.5-mL Eppendorf tube; 8 PCR reactions were collected in each 1.5-mL tube. To remove any remaining mineral oil, each sample was extracted with an equal volume (400 mL) neutral phenol/chloroform (1:1 v/v) solution. The aqueous layers were transferred to clean tubes and precipitated with 800 mL 95% ethanol by freezing at −20° C. for at least 30 min. Samples were resuspended in a total volume of 240 mL sterile deionized, distilled water and mixed with 40 mL 5×loading buffer (Sambrook et al., 1989). The DNA fragments representing the 16S rRNA PCR product were separated on a 0.8% ultrapure agarose (ICN, Aurora, Ohio) gel run at 100V (approximately 5 V/cm).

A DNA fragment was detected at approximately 1.4 kilobases (kb); this was excised with a razor and removed from the agarose using the Geneclean™ kit (BIO 101, Vista, Calif.). For this procedure, agarose gel bands approximately 1.5×0.5×0.5 cm were placed in sterile 1.5-mL Eppendorf tubes and dissolved in 900 mL Geneclean NaI solution at 55° C. for 10 min. DNA was extracted onto glass beads by adding 10 mL Geneclean glass milk solution, mixing by inversion, incubating at room temperature for 10 min, centrifuging at maximum speed for 5 s and discarding the supernatant. The glass bead and DNA pellet was washed three times by resuspending in 300 mL Geneclean New Wash buffer, centrifuging 5 s and discarding the supernatant. After the final wash step, the pellet was air dried for 10 min and resuspended in 20 mL sterile deionized, distilled water by adding a 10 mL portions of water, resuspending the glass beads, warming to 55° C. for 10 min, then centrifuging 30 s and collecting the water two times. The DNA concentration was measured by fluorometry; if the sample was not concentrated enough for sequencing (200 mg/mL) then the remaining DNA preparation was precipitated by adding 60 mL 95% ethanol, freezing at −20° C. for at least 30 min. centrifuging 10 min, discarding the supernatant and air drying the DNA pellet, which was resuspended in the appropriate amount of sterile deionized, distilled water to provide a sample for sequencing. Samples were checked by electrophoresis on a 0.8 agarose gel as well as measuring their DNA concentration by fluorometry.

Sequencing of the 16S rRNA gene fragment: The 1400 bp DNA fragment generated by PCR of *P. polymyxa* genomic DNA using primers 8F and 1403R was sequenced. Samples were submitted for sequencing in the form of PCR product (template) as 5 mL of a 200 mg/mL solution in sterile deionized, distilled water and primers (each separately at a concentration of 3 pmol/mL in sterile deionized, distilled water).

BLAST search protocol: The *P. polymyxa* PKB1 16S rRNA sequence was submitted to the basic local alignment search tool (BLAST) sequence alignment system. This search tool was developed by the National Center for Biotechnology Information (USA). The BLAST search tool provides a sequence database for DNA, RNA and proteins (Peruski, L. F. Jr. and Peruski, A. H. 1997. The Internet and the New Biology: Tools for Genomic & Molecular Research, American Society for Microbiology, Washington, D.C. pp. 52–59). The web site for this is http://www.ncbi.nlm.nih.gov, and the reference for its use is Altschul et al. (Altshul. S. F., Madden, T. L., Schäffer, A. A., Zhang, J., Zhang Z., Miller, W. and Lipman, D. J. 1997. Gapped BLAST and PSI-BLAST: A new generation of protein database search programs. Nucleic Acids Research. 25: 3389–3402). An advanced ungapped BLAST search with an expect of 10 was used. A total of 10 identities were checked to ensure that the sequences the WPW-S28 sequence was compared with were >1000 bp in length.

Figure 1B:
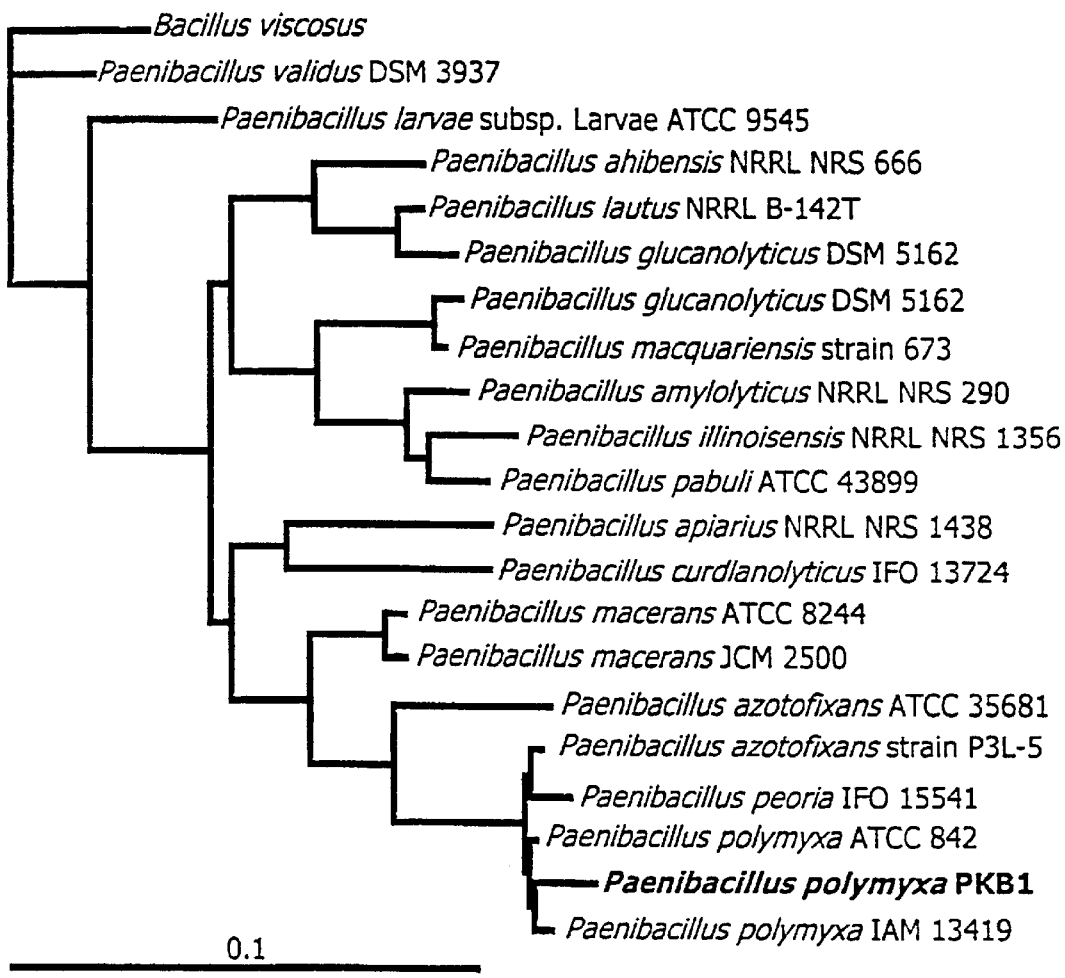
FIG. 1B is a phylogenetic tree diagram showing the relatedness of *P. polymyxa* PKB1 to other gram positive bacteria with known 16S rRNA sequences. Relatedness was determined using RDP and the tree diagram was made using a software program called Treeview™.
Figure 2:
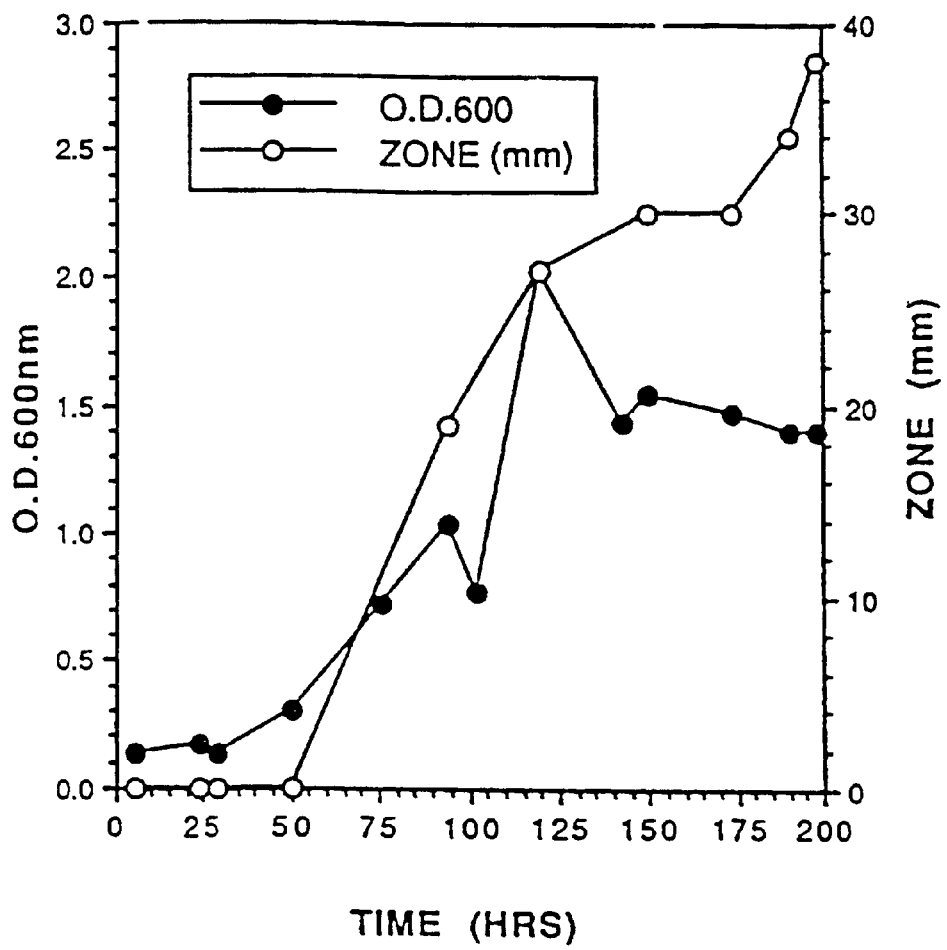
FIG. 2 is graph showing the growth curve and the antibiotic production of PKB1 at 10° C.

Ribosomal database project search protocol: The *P. polymyxa* PKB1 16S rRNA sequence was submitted to the Ribosomal Database Project (RDP) for sequence alignment and for the generation of a specific phylogenetic tree (Maidak B. L., G. J. Olsen, N. Larson, R. Overbeek, M. J. McCaughey and C. R. Woese. 1997. The RDP (ribosomal database project). Nucleic Acids Research. 25, 109–110.). The web site for the RDP was formerly http://rdpwww.life.uiuc.edu/; the new site is http:www.cme.msu.edu/RDP. Both were used for this project. A phylogenetic tree showing the results of the study is shown in FIG. 1B.

II. Establish Cultivation Conditions That Optimize the Production of the Antifungal Antibiotic The *P. polymyxa* strain of the present invention was originally isolated and observed to inhibit *L. maculans* when grown on potato dextrose agar plates (PDA). This medium has a pH of 5. Most bacteria grow better in less acidic conditions, so a search for a medium that allowed optimum growth and antibiotic production was undertaken. Many different kinds of both complex and defined media were used as growth substrates for the antifungal antibiotic producing *P. polymyxa*. Potato dextrose broth with added nutrients was also tested. Temperature and aeration were varied in order to determine the optimal growth conditions. Inoculum size and pH of the medium were also tested for their effect on antibiotic production. Scale-up cultures for use in 15 liter fermenters were tested to determine whether the organism could produce antibiotic in large quantities. Growth of the bacterium in broth culture was measured by determining the optical density (OD) of the culture at 600 nm with a spectrophotometer at regular time intervals during the growth cycle. The life cycle of the bacterium was recorded at the same time by making wet mount slides from the broth culture and viewing at 400×magnification under a microscope. Antibiotic production by the culture, was measured using a plate bioassay with *L. maculans* as the indicator organism. For the bioassay, the antifungal antibiotic was extracted from culture pellets with 100% methanol and placed into wells scored into the agar of the bioassay plate. After 48 h, a zone of inhibition in the lawn of fungus was seen indicating that the sample contained antifungal antibiotic.

Culture conditions were varied to determine an optimal medium and optimal growth conditions for the production of the antifuingal antibiotic. The optimization of conditions was based on the assumption that the amount of and the stage of growth and antibiotic production were directly related. Rich media that can support much bacterial growth like nutrient broth, beef extract broth, and Landry's medium were tested and the resulting growth and antibiotic production was compared to potato dextrose broth (PDB). Bacterial growth increased on rich media but antibiotic production decreased; the amount of antibiotic produced could not be increased by simply increasing bacterial growth. To determine whether a specific nutrient affected antibiotic production PDB was supplemented with varying quantities of other nutrients. The growth and antibiotic production results were compared to those of bacteria grown in unmodified PDB. The type and quantity of carbon source needed for optimal antibiotic production was tested by adding these compounds to PDB; glucose, sucrose, dextrose, starch, soy meal and different amino acids. The type and quantity of trace vitamins and minerals needed for optimal antibiotic production were also tested by adding these to PDB; biotin, ascorbic acid, sodium nitrate, potassium phosphate, sodium sulphate and magnesium sulphate. Some of these nutrient combinations increased the antibiotic production of the P. polymyxa strain PKB1, but not in a reproducible manner. The amount of antibiotic production of P. polymyxa in PDB and in potato dextrose agar (PDA) was consistently high so these media was selected for growth of the bacterium. The rate of aeration, pH of the medium and growth temperature were also tested to determine optimal growth conditions. In small scale shake flask experiments antibiotic production was optimized at 200 ml PDB in a 500 ml Erlenmeyer flask with shaking of the culture at 200 rpm. For bioreactor growth, 10 L of PDB in a 15 L fermentation tank with agitation set at 200 rpm were the conditions that met with optimum growth of the bacterium. Bacterial growth required a starting pH of 6.5. However, as the growth of the bacterium progresses the pH drops to about 5. Antibiotic activity was detected after the medium reached a pH of 4.6 to 5. This strain of *P. polymyxa* can grow in a temperature range of 10° C. to 35° C. Bacterial growth was slower at lower temperatures, however the quantity of antibiotic produced was not affected by temperature. Growth and antibiotic production for the isolate were monitored over time. Shortly after exponential growth ceased (30 to 35), the cells entered a dormant spore stage: at this point the antibiotic activity was first detected (FIG. 2).

III. Purify and Characterize the Antifungal Antibiotic Produced by Strain PKB1

Bacillus spp. are well known for their production of peptide antibiotics. *P. polymyxa* in particular makes a family of closely related small peptide antibiotics called polymyxins. The purification protocol developed took into consideration that this antibiotic might be a small protein, between 2 to 20 amino acids, like the polymyxains. Commercially obtained polymyxins were ineffective against *L. maculans*. The PKB1 bacterium does not appear to produce polymyxins since it could not inhibit any of the bacteria that polymyxin producing *P. polymyxa* strains can. Therefore, although the antibiotic peptide according to the present invention may be similar in structure, it was determined not to be one of the known polymyxins. Preliminary, purification experiments showed that the antibiotic was associated with the cell or spores rather than with culture broth.

Cells were harvested by centrifuigation. Antibiotic was extracted from either fresh cultures or from freeze dried spore stocks. Antibiotic was initially extracted from the Paenibacillus strain into 100% methanol. Successful extraction of the antibiotic was also achieved using 0.1% acetic acid. However most of the work was done using methanol. A small scale purification protocol was designed because pure antibiotic was only required for characterization which typically involves small amounts of sample. The purification steps were also regulated by the need for techniques that were compatible with organic solvents. The primary methanol extract was condensed to 2 ml by rotary evaporation and centrifuged. The supernatant was loaded onto a Sephadex LH-20 (Pharmacia) gel filtration column which was equilibrated and eluted using methanol. Active fractions were collected and condensed to 3 ml. This active sample was made into a 50% methanol solution by adding 3 ml of distilled water and was loaded onto a Sep-Pak C-18 reverse phase cartridge (Millipore-Waters). The activity was eluted from this cartridge with methanol and found in 5 consecutive fractions of 1 ml each. Active fractions were dried under nitrogen. The white precipitate was resuspended in acetonitrile:water (1:3) containing 0.1% NaH $_2PO_4$ and loaded onto a μBondapak C-18 (Millipore-Waters) reverse phase HPLC column. The components were eluted using a gradient mobile phase of (A) acetonitrile:water (1:3) containing 0.1% $NaH_2PO_4$ and (B) acetonitrile.

In another procedure, *P. polymyxa* PKB1 was grown in a 10 liter fermenter in PDB. Cells were harvested after sporulation and freeze dried. Antibiotic samples were extracted from 1 gram of freeze dried spores. The spores were rinsed with water, resuspended in 60 ml of 100% HPLC grade methanol and left to sit for 60 minutes. The spores were then pelleted by centrifugation and the methanol supernatant saved. This crude antibiotic extract was condensed to 3 ml by rotoevaporation and the extract was periodically filtered using a 0.45 μm μstar filter from Costar (Fisher Scientific. Ontario, Canada).

The condensed crude extract was loaded onto a Sephadex LH-20 gel filtration column, using the same method as noted above and a mobile phase of 100% methanol at a flow rate of 0.2 ml/min. Fractions were collected every 10 minutes and the absorbance of the fractions at 280 nm was recorded. The active fractions eluted between 130 and 190 minutes.

The active fractions from the Sephadex column were condensed to 5 ml and loaded onto a reverse phase Sep-Pak C18 column in 50% methanol. The antibiotic was eluted from this column using 100% methanol at a flow rate of 1.2 ml./min. The active fractions were dried under nitrogen. The dried sample was resuspended in 200 μl of acetonitrile:water (1:3) plus 0.1% $NaH_2PO_4$ and loaded onto the reverse phase C18 HPLC. The mobile phase was a gradient of acetonitrile:water (1:3) plus 0.1% sodium dihydrogen orthophosphate and acetonitrile. The acetonitrile was ramped in a 0% to 60% linear gradient over 2.5 minutes, held for 10 minutes, followed by a further linear gradient from 60% to 100% over 37.5 minutes, held for 10 minutes, then ramped down to 0% by 65 minutes. The active fractions were eluted from 9 to 15 minutes.

Purity of the active fractions generated throughout purification was monitored by three methods: 1) plate well bioassay, 2) sodium dodecyl sulfate-polyacrylamide gel electrophoresis (SDS-PAGE) on 16.5% acrylamide gels run in tricine buffer and 3) bioautography. The plate well bioassay was as described in example II. The 16.5% acrylamide tricine SDS-PAGE was designed to separate peptides and small proteins with molecular weights as low as 2 kD. Coomassie blue was used to stain gels to detect the presence of peptides or proteins. The bioautograph detects the presence of antifungal activity from peptide bands on the gel. After SDS-PAGE, the gel was washed in water and then placed on the surface of a bioassay plate. Soft agar inoculated with the indicator organism was poured over the gel and allowed to solidify. If there is any antibiotic in the gel it diffuses into the agar of the bioassay plate. In so doing, it inhibits the indicator organism and a zone of inhibition results.

The antibiotic was characterized by amino acid composition analysis and mass spectroscopy. The mass spectrum was measured by two methods, one using glycerine/thioglycerol matrix fast atom bombardment spectroscopy and the other by metastable analysis which is a type of double mass spectroscopy called MS-MS. The peptide was further characterized by measuring its stability at a range of temperatures over time, its reaction to proteases, ester hydrolysis, coloration reactions with ninhydrin and other dyes and stains, solubility in a variety of solvents and the inhibitory spectrum towards a variety of fungi and a limited number of bacteria.

The first step in the purification process was chromatography of the methanol extract on a Sephadex LH-20 gel filtration column, to separate components on the basis of size and their affinity toward methanol as the mobile phase. Extract components were monitored at the time of elution by measuring the effluent absorbance at 280 nm. This wavelength can detect certain amino acids such as tyrosine and tryptophan. The absorbance profile indicated that the fractions with antifungal activity still contained contaminating components because it contained two broad peaks. Active sample was then passed through a Sep-Pak cartridge, a small scale reverse phase column that separates components on the basis of polarity such that more polar components elute first. The antibiotic is one of the first components to elute from the column, suggesting that it is relatively polar. The antibiotic containing fractions were then run on a reverse phase HPLC column and the resulting effluent monitored for absorbance at 214 nm to detect materials containing peptide bonds (FIG. 3). The fractions were tested for activity using the well bioassay method and the activity profile was compared to the HPLC absorbance trace. The presence of the antifungal peptide was monitored during the purification procedure by a well bioassay and by a bicinchoninic acid assay (BCA) that measures the protein concentration in the sample (Table 1A).

TABLE 1A

The antifungal activity and amount of protein in the antibiotic extract throughout the purification procedure.

| PURIFICATION STAGE | ZONE OF INHIBITION (MM) | AMOUNT OF PROTEIN (MG) |
|---|---|---|
| Primary methanol extract | 35 | 90 |
| Active fractions from Sephadex LH-20 | 36 | 7.5 |
| Active fractions from Sep-pak column | 32 | 3.2 |
| Active fractions from RP-phrase | 26 | 1.7 |

Preliminary characterization of the active material to determine its approximate molecular weight was performed using ultrafiltration with membranes of molecular weight cutoffs 10,000, 3,000 and 2,000 Daltons. Activity was found in the 2,000 Da eluent suggesting that the molecular weight is between 1–2000 Da, consistent with the active material being a small peptide. The molecular weight of the antibiotic was further estimated using a polyacrylamide gel electrophoresis system containing 16.5% acrylamide that is designed to separate low molecular weight components (FIG. 4). The antifungal activity was found in a band corresponding to a standard molecular weight marker of 2.3 kDa by using the SDS-PAGE in a bioautograph (FIG. 5).

Another preliminary characterization of the antifungal antibiotic was performed by using an acid hydrolysis technique coupled to thin layer chromatography (TLC) and ninhydrin coloration. Ninhydrin reacts with amine groups, forming a colored derivative. Any free amine groups such as in amino acids or at the amino terminal (NT-terminal) of linear, unblocked peptides or proteins will react. Acid hydrolysis breaks the peptide bonds between amino acids in a peptide or protein. The active fraction was acid hydrolyzed, run on TLC and the TLC plate sprayed with ninhydrin. An unhydrolyzed active fraction was run on TLC and sprayed with ninhydrin at the same time. The hydrolyzed sample showed ninhydrin positive spots, indicating the presence of amino acids, whereas the material which had not been treated by hydrolysis gave no ninhydrin reaction. This suggests that the active fraction is made up of amino acids but that the unhydrolyzed form of the antibiotic is either a cyclic or an N-terminally blocked peptide.

The peptide could not be successfully sequenced by the Edman degradation method. In this method the N-terminal amino acid is derivatized by a chemical and the peptide bond between it and the next amino acid is cleaved. This frees the derivatized amino acid from the rest of the peptide so it can be characterized by chromatography after comparison to amino acid standards. In this way, the sequence of amino acids can be determined since they are cleaved from the peptide one by one. That the Edman degradation was unsuccessful shows that the N-terminal is either blocked by a chemical modification or it is involved in a peptide bond, making the peptide cyclic.

The antibiotic was incubated with carboxypeptidase A over a 3 hour time period and the activity measured by a well bioassay. Carboxypeptidase A cleaves the peptide bond joining the last amino acid at the carboxy terminus to the rest of the peptide. It will continue cleavage of the carboxy terminal amino acid until there is no more substrate available. If there was a carboxyl terminal amino acid available for the protease to use as a substrate on the antibiotic then the antifungal activity of the sample would disappear. The sample remained active after carboxypeptidase A protease treatment, suggesting that there is no C-terminal amino acid available, probably due to the peptide being cyclic.

The temperature stability of the antibiotic was measured at −70° C., 4° C., 25° C. and 100° C. The antibiotic retained its activity after 30 min at 100° C. 3 weeks at 25° C. 4 month at 4° C. and indefinitely at −70° C.

The antibiotic is soluble in methanol, ethanol, acetonitrile, propanol and acetic acid and slightly soluble in water.

The antifungal activity of the antibiotic had been tested against fungi other than *L. maculans* and against some bacteria. The fungi that were inhibited by this antibiotic include: *Aspergillus niger*, Sporobolomyces sp., *Pythium pythioides*, Trichoderma sp., *Penicillium chrysogenum, Penicillium roquefortii, Sclerotinia sclerotiorum, Rhizoctonia solani, Fusarium avenaceum* and *Alternaria brassicae*. The antibacterial spectrum of this antibiotic is limited because not many bacteria have been tested however some bacteria have been found to be sensitive to this antibiotic, including: *Micrococcus luteus, Streptomyces clavuligerus* and *Escherichia coli* ESS.

TABLE 1B

The inhibition profile, solubility and stability of the antifungal antibiotic.

| | |
|---|---|
| INHIBITION PROFILE | *L. maculans*, Sclerotinia sp., Fusarium sp., Alternaria sp., *Micrococcus luteus, Rhizoctonia solani* |
| SOLUBLE | methanol, ethanol, dimethylsulfoxide. acetonitrile:water (2:1) and (1:3) |
| INSOLUBLE | acetone, n-hexane methylene chloride |
| SLIGHTLY SOLUBLE | water |

TABLE 1B-continued

The inhibition profile, solubility and stability of the antifungal antibiotic.

| | |
|---|---|
| NINHYDRIN REACTION | negative |
| Rf TLC: butanol; acetic acid: water | 0.9 to 0.95 |
| PROTEASE TREATMENT | resistant to cleavage |
| STABILITY | 100° C. for 30 minutes |
| | 4° C. for 6 weeks |

The mass spectrum of the peptide antibiotic was first taken using a gentle ionization method so as to not fragment the sample. This spectrum showed that the active material consisted of two components, one with a molecular weight (MW) of 883.5 and the other at 897.5 (FIG. 6A). The two components could not be two fragments of a larger component since the gentle ionization procedure was followed. These two components were investigated further by taking a mass spectrum of the sample using the metastable technique and a mass spectroscopy method that employs two mass spectroscopy instruments linked in tandem. It allows for a sample containing two components to be separated by holding one of the components at the first MS and fractionating the other component through the second MS. By fractionating the components separately and comparing the fragments generated, the similarity between the two components could be determined. Peptides will fractionate at certain sites in a reproducible manner, therefore the same structure will fractionate in a reproducible manner. The fragmentation patterns for the two components were identical, indicating that these two components are the same. However, it is known that there must be some chemical modification between the two components since they are of different molecular weights.

Post source decay (PSD) mass spectroscopy was used to determine the amino acid composition of each of the two components. The composition for the component having a molecular weight of 883.5 is listed in Table 2.

TABLE 2

The amino acid composition of the 883.5 MW antifungal antibiotic.

| AMINO ACID | QUANTITY IN PEPTIDE |
|---|---|
| glutamic acid | 1 |
| aspartic acid | 2 |
| threonine | 1 |
| acetyl-modified leucine | 1 |
| alanine | 1 |
| proline | 1 |
| valine | 1 |
| TOTAL | 8 |

The PSD mass spectra indicated that the peptide was a branched ring with a side chain of N-acetylleucine and valine on a threonine in the ring. Although it is known that the ring contains threonine (1 mol), aspartic acid (2 mols), alanine (1 mol), glutamic acid (1 mol) and proline (1 mol), the exact sequence of these amino acids in the ring are not known. One postulated structural formula is shown in FIG. 6B.

The PSD data for the 897.5 MW component indicated that it also contained eight amino acids corresponding to the composition of the 883.5 MW peptide, except that it contains isoleucine instead of the valine.

The PSD data also indicated that there were other similarly sized peptides which were extracted from the spores of the *Paenibacillus polymyxa*, strain PKB1 including peptides having molecular weights of 912, 914, 920, 928, 942. The differences between the other five peptides when compared to the 883.5 MW peptide is that there is probably a isoleucine in one of them instead of the valine or another valine instead of the alanine that is in the 883.5 peptide or that both of the aspartic acid residues are glutamic acid residues in one of the minor peptides when compared to the structure of peptide 883.5.

The antibiotic components do not appear to be ribosomally produced but rather produced by peptide synthetase activity.

IV. Determine Whether *Paenibacillus polymyxa*, Strain PKB1 Could be Used as an Agent for Biocontrol of Blackleg on Canola Crops

*Paenibacillus polymyxa*, strain PKB1 has two properties that make it an attractive biocontrol agent. First, it is a native soil bacterium and, second, it can form dormant spores. Effect of strain PKB1 on *L. maculans* pycnidiospore germination and viability was studied. A loopful of *P. polymyxa* from an actively growing culture was transferred to 5 ml of nutrient broth and incubated at room temperature for three days. A bacterial suspension was then prepared in sterile distilled water and adjusted to approximately 1×10 cells $ml^{-1}$. Fresh pycnidiospore suspension of a virulent strain of *L. maculans* was prepared using a 10 day old fungal culture grown on V-8 juice-Rose Bengal agar amended with streptomycin sulfate (200 ppm). The suspension was adjusted to $1\times10^6$ pycnidiospores $ml^{-1}$.

Effectiveness of the bacterium in inhibiting pycnidiospore germination was tested in Petri plates. A piece of autoclaved cellophane membrane was placed on the surface of 2% water agar in a nine cm-diameter petri plate. Thereafter, 0.5 ml of pycnidiospore suspension and 0.5 ml the bacterial suspension, each alone or in a mixture, was spread on top of the membrane. Each treatment was applied to four replicated plates which were incubated at room temperature (23° C.) under cool white fluorescent tubes and incandescent lamps (300 $mEm^{-2}S^{-1}$). A small piece of cellophane was cut from each plate every 24 h for three days, mounted on a microscope slide, stained with lactophenol cotton blue and observed with a compound microscope. The percentage of germinated pycnidiospores and length of germ tubes were recorded. The experiment was repeated once.

The percentage of *L. maculans* pycnidiospore germination and average germ tube length were significantly and substantially reduced by the presence of *P. polymyxa* (Table 1).

TABLE 3

Effect of *Paenibacillus polymyxa* strain PKB1 (B) on germination and germ tube length of pycnidiospores of *Leptosphaeria maculans* (BLA).

| | Percent pycnidiospore germination* | | Average germ tube length (μm)** | |
|---|---|---|---|---|
| Day | BLA + B | BLA | BLA + B | BLA |
| 1 | 12.25a | 79.50b | 3.905a | 11.835b |
| 2 | 18.25a | 96.50b | 8.595a | 15.165b |
| 3 | 23.50a | 98.50b | 9.625a | 83.665b |

*Based on 400 pycnidiospores
**Average of 100 spores

Means within individual rows followed by the same letter are not significantly different as determined by Tukey's Studentized Range Test (P=0.05).

Initially, some pycnidiospores germinated but germ tube extension was significantly inhibited as the experiment progressed, perhaps in response to an inhibitory substance released by bacteria.

Scanning electron microscopy was used to determine if morphological changes occurred in pycnidiospores after treatment with the bacterium. Pycnidiospore and bacterial suspensions were sprayed on cellophane membranes, as described above, or on intact canola leaves. To inoculate leaves, canola (*B. napus* cv. Westar) seeds were planted in 15 cm pots in a growth chamber (20° C. 12 h light). Two weeks after planting, intact canola leaves were sprayed with *L. maculans* pycnidiospores alone or mixed with a bacterial cell suspension. Plants were covered with a plastic bag to maintain high humidity for 2 days, and incubated in the growth chamber. After 24, 48 and 72 h of incubation, leaf and cellophane samples were vapor fixed by osmium tetroxide and frizzed for 15 min in liquid nitrogen at solid point (−27° C.) in a cryo-stage (Emitech K1250), held 30 min at −40° C. to thaw ice crystals at SEM vacuum stage, and then were gold coated at −178° C. in a cryo-stage chamber. Prepared specimens were then examined using a scanning electron microscope (SEM) (JSM-6301F).

SEM studies showed that there were no obvious morphological changes on the surface of pycnidiospores treated with the bacterial suspension (FIG. 7). Both, fungal pycnidiospores and bacterial cells were heavily covered with mucilaginous materials. Pycnidiospores surrounded by the bacterial cells exhibited reduced germination and poor germ tube growth. The SEM study revealed that strain PKB1 does not cause visible changes to the fungal cell wall components, and that pycnidiospore inhibition is most likely due to an antifungal metabolite that interferes with pycnidiospore metabolism.

To determine viability of the pycnidiospores in the presence of strain PKB1, a mixture of *L. maculans* pycnidiospores and bacterial cells was incubated at room temperature for 2 days and stained with FungoLight fluorescent dye (25 ul/ml, Molecular Probe, Oregon, U.S.A.) for 30 min at 37° C. An unamended pycnidiospore suspension was also stained for comparison. Five microliters of each cell suspension was trapped between a microscope slide and a cover slip and examined under a fluorescent microscope at 530 nm.

Pycnidiospores mixed with the bacterial suspension fluoresced dull yellow when treated with FungoLight, indicating reduced viability; pycnidiospores not treated with bacteria fluoresced bright yellow with a red cylindrical object inside each cell.

Media: All broth and agar media were from Difco.

Growth Curves: Starter cultures for the growth curve experiments were grown in tryptic soy broth with 1.0% soluble starch (TSB), 25 ml in a 125 ml Erlenmeyer flask, grown for 24 h at room temperature, 200 rpm. A 1.0% inoculum of *P. polymyxa* glycerol spore stock was used. The growth cultures were grown in potato dextrose broth, 200 ml in a 500 ml Erlenmeyer flask, at 200 rpm. A 2% inoculum of *P. polymyxa* from the starter culture was used. The growth temperature was either 10° C., 21° C. or 30° C. Growth was monitored by turbidity measurements in a UV/VIS spectrophotometer at 600 nm and by microscopic examination at 400×magnification.

Micro Antibiotic Extraction: To monitor the antibiotic production during a growth assay, 1.5 ml sample was taken from the culture, the cells were harvested by centrifugation at 13.000×g for 5 min and the supernatant was saved for measurement of the culture pH. The cell pellet was resuspended into 200 ul of methanol for 20 min and then the cells were pelleted again and the methanol extract was assayed for antibiotic activity in a well bioassy.

Macro Antibiotic Extraction: The cells in 200 ml of culture broth were pelleted at 10,000×g for 20 min and the supernatant was discarded; alternatively 1 gram of freeze dried cells was used. The cells were washed once with distilled water and then resuspended into 60 ml of methanol and held for 1 hour. The resuspended cells were pelleted by centrifugation and the methanol extract (referred to as primary methanol extract) was used in the antifungal antibiotic purification protocol.

Fermentation and Freeze-drying: Fermenters were used to grow 10, 30 and 50 liter batches of *P. polymyxa*. PDB was used as the growth medium and 5 and 2.5% inocula from TSB starter cultures were used to initiate growth. Aeration was regulated at 15 L/min. temperature at 26° C. and the cells were harvested after sporulation. The cell pellet was resuspended into a small volume of sterile distilled water and lyophilized.

Well Bioassay: 100 ml of molten potato dextrose agar (PDA) was poured into 15×15 cm bioassay plate. After solidification 800 ul of *L. maculans* pycnidiospores in 20% glycerol were spread on the surface as the indicator organism. 10 mm diameter wells were cut from the plate with a sterile cork borer and 75 ul amounts of sample were placed in the wells. The diameters of the zones of inhibition of the fungus around the well are measured in millimetres after 24 h incubation at room temperature.

BCA Assay: An assay kit from Pierce Chemicals was used as the source of reagents and protein standards. The standard protocol methods designed by this company are used. A standard curve was generated using bovine serum albumin and the unknown samples were compared to this for identification of the protein concentration.

Sephadex LH-20 Chromatography: After the primary methanol extract was condensed to 2 ml from 60 ml by rotary evaporation, it was loaded onto a Sephadex LH-20 column(2.5×25 cm). The column was equilibrated and eluted at 4° C. using methanol as the mobile phase at a flow rate of 0.2 ml/min. Ten minute fractions were collected and assayed for absorbance at 280 nm and for the presence of antibiotic by bioassay. The activity is found in fractions 13 to 19.

Sep-Pak Chromatography: The pooled active -fractions from the Sephadex chromatography were condensed by evaporation under nitrogen to 5 ml from 14 ml. The fraction was diluted to 50% methanol and loaded onto a Sep-Pak CA8 cartridge (Millipore Waters). This is a small reverse phase $C_{18}$ column. The active fraction was eluted with methanol at a flow rate of 1.2 ml/min and 1 ml fractions were collected. Activity was found in fractions 3 to 7.

Reverse Phase HPLC: The pooled active fractions from the Sep-Pak were condensed to dryness under nitrogen and redissolved into 200, 400 or 600 ul of mobile phase liquid. The sample was loaded onto a uBondapak C-18 RP-HPLC column (Millipore Waters) and eluted with one of two different mobile phase gradients at a flow rate of 10 ml/min collecting one min fractions. One gradient was (A) acetonitrile: water (1:3) containing 0.1% $NaH_2PO_4$ and (B) acetonitrile with the gradient varying from 0 to 100% (B) over 90 min. The other gradient varied from 0 to 60% (B) over 5 min, held at 60% (B) for 10 min. increased to 100% (B) over 35 min and then decreased to 0% (B) over 5 min. The antibiotically active material was found in fractions 61 to 63 with the first gradient and in fractions 19–20 with the second gradient. 16.5% Acrylamide SDS-PAGE: This is a high percent acrylamide gel using a tricine running buffer to separate small molecular weight proteins/peptides. 80 ul volumes of sample were loaded into the wells and the gel was electrophoresed for 16 h at 80V. The peptides were visualized by staining the gel with Coomassie blue.

Bioautograph: Following SDS-PAGE, the gel was washed in distilled water and then placed onto solidified PDA in a bioassay plate. Soft PDA was inoculated with 500 ul of *L. maculans* pycnidiospores and then poured over the gel and allowed to solidify. Antibiotic will elute from the gel and enter the PDA where it can inhibit the fungus and cause a zone of inhibition that correlates to where the antibiotic migrated to in the gel during electrophoresis.

V. Detection of Molecular Polymorphism Within and Among *Paenibacillus polymyxa* and Bacillus spp.

Twenty-three isolates from *Paenibacillus polymyxa* and seven Bacillus spp. Were obtained. DNA polymorphism was determined using RAPD-PCR technique. Another 64 bacterial isolates from canola stubble and compost from canola fields were collected and used to test the developed probes.

Genomic DNA was extracted generally according to the procedure described by Sambrook et. al. (Sambrook, J. E. et. al. Molecular cloning: A Laboratory manual. 2nd Ed. Cold Spring Harbor Laboratory Press, NY 1989).

Two strains of the bacteria were amplified with twenty random primers (Operon Technologies Inc., Alameda, Calif. U.S.A.) in a preliminary study. Four of these 20 primers were selected for further use because these produced good and countable bands. PCR reactions were carried out in a thermal cycler (Thermolyne. Temp. Tronic, Barnstead/Thermolyne Corporation, Dubuque, Iowa, U.S.A.). The amplified products were run electrophoreses in 1% agarose gels, stained with ethidium bromide and photographed under UV light. One kb DNA ladder (Gibco-BRL) was used as a DNA size marker. All reactions were performed twice.

DNA of PKB1 was amplified with primers OPA07, OPA08, OPA13 and OPA14. Four DNA fragments of 0.61, 0.71. 0.27 and 0.62 kb were excised from agarose gel of PCR products amplified with each primer respectively and purified with DNA Purification Kit (Boehringer Mannheim Corp.). The purified DNA fragments were separately labeled with alkali labile Dig-11-dUTP in a simultaneous amplification in a thermocycler by using the same PCR profile as described previously. Estimation of the yield of Dig-labeled probe was done according to the method of Genius System User's Guide for Membrane Hybridization. Version 3.0 (Boehringer Mannheim Corp.). The probes were stored at −20° C. for later use.

The cenomic DNA of 23 Bacillus and Paenibacillus strains was digested with restriction endonucleases. EcoRI, PstI, and HindIII (Gibco-BRL) separately at 37° C. for 1 h. The DNA digests were electrophoresed on 1% agarose gel. A 21 kb dig-labeled marker (Boehringer Mannheim Corp.) was used.

The Southern hybridization was carried out following the procedure described by Sambrook et al. (1989) and Genius System User's Guide for Membrane Hybridization, Version 3.0 (Boehringer Mannheim Corp.).

Probed DNA was detected with CSDP (disodium 3-(4-methoxyspiro [1,2-dioxetane-3,2'{5'-chloro}tricyclo(3,31, 1$^{3.7}$)decan[-4-yl)phenyl phosphate) using a DIG Luminescence Detection Kit (Genius 7, Boehringer Mannheim Corp.). The membrane was exposed to X-ray film (Fuji) for 2–3 h at room temperature and the image on the film was scanned into a computer and analyzed using a molecular analysis program.

The specificity of the probes was also determined by dot blotting method using 23 known *P. polymyxa* and Bacillus strains and 64 unknown bacterial strains.

Four DNA probes were cloned on *Escherichia coli* supercompetent cells using a pCR-Script™ SK(+) Cloning Kit (Stratagene Inc.) and the plasmid DNA was extracted using a PlasmidPURE™ DNA Miniprep Kit (Sigma Bio Sciences™). The yield and quality of the purified plasmid DNA was examined by electrophoresis on 1% agarose gel. To check for the insert, the plasmid DNA was digested with restriction endonuclease KpnI and SacI at 37° C. for 1 h. The digests were electrophoresed on 1% agarose gel and stained with ethidium bromide.

Confirmed plasmid DNA with insert was sequenced (ABI Prism). Two universal primers T3 and T7 were used. The data were edited and analyzed using a computer software GeneJockey™.

Amplification patterns of 23 strains of *Paenibacillus polymyxa* and seven different Bacillus species with four primers, OPA07, OPA08, OPA13 and OPA14, are given in FIG. 8. In FIG. 8:

1. Isolates 96-1 and 97-1 are the two subcultures of the original isolate of *Paenibacillus polymyxa* (Strain PKB1). Strains 96-2 to 96-5 were isolated from canola stubble that were buried in soil after treatment with compost infested with the strain PKB1. These strains seem to be the isolates of PKB1 strain as these have identical DNA pattern.
2. Isolates R-1 and R-2 are the two antibiotic resistant mutants of PKB1 that were developed in the laboratory. These are also similar to the patterns of other PKB1 strains (96-1 to 96-5).
3. 97-2 is Colistinus Koyama strain of *Paenibacillus polymyxa* available from ATCC. 97-3 is NCIB 4686 strain, a type strain of *Paenibacillus polymyxa*. DNA patterns of both 97-2 and 97-3 are different from PKB1 (Strains 96-1 to 96-5 and R-1 and R-2).
4. The remainder of the DNA patterns are of Paenibacillus and other Bacillius species obtained from Dr. Richard Coleman, ARC, Vegreville, or other colleagues elsewhere.

The PCR results show that PKB1 is a novel strain of *Paenibacillus polymyxa*.

These four primers gave multiple products in the 0.3–6 Kb size range. OPA13 gave fewer products but very clear amplification patterns (FIG. 8C). When these four primers were used, all the strains in a particular group showed one or two fragments in common for each primer. Strains 1 to 8 produced antifuingal substance and were originated from the same source, whereas strains 9 to 13 were from different locations. Strains 14 to 23 were from seven different Bacillus species.

All four probes (P1–7, P1–8, P1–13 and P1–14) used to hybridize with the Southern blots of HindIII, EcoRI and PstI restriction digests were species specific and only hybridized with DNA or PKB1 and the related strains of the specific Paenibacillus species (strains 1–11 in FIGS. 9A, 9B and strains 1–13 in FIGS. 9C–F) but not with that of other Bacillus species (strains 14–22 in FIGS. 9C–F).

DNA of the antibiotic resistant bacterial mutants could also be probed (isolates 12 and 13 in FIGS. 9C–F). DNA of the bacterial isolates from compost was tested in Southern blot hybridization but none of them could be probed (strains 12–22 in FIGS. 9A and 9B).

Probes 1–7 and P1–8 were used to detect the DNA of bacterial strains with dot-blotting method. PKB1 and all related strains in the specific Paenibacillus sp. could be probed (FIGS. 10A and 10B). This is confirmed that the probes are species specific. Once the specific probe is developed, dot-blot method is very simple and easy to be used in the detection of the bacterium.

DNA of four probes were cloned and sequenced with the length of 609 bp (p1–7), 713 bp (P1–8), 270 bp (P1–13) and 617 bp (P1–14). Two sequences could be translated into polypeptides with no interruption stop codons in some reading frames. One sequence has some identity with the protein required to initiate sporulation in a Bacillus sp. The other has some identity with an enzyme produced by a Paenibacillus sp. Genetic markers of this bacterial strain were determined by randomly amplified polymorphic DNA-polymerase chain reaction (RAPD-PCR). Four DNA fragments, specific for PKB1, were selected for making probes. The four probes were used to hybridize with Southern blots of EcoRI, PstI, and HindIII restriction digests of 23 strains of *Paenibacillus polymyxa* and seven Bacillus sp. The probes were species specific and hybridized only with DNA of PKB1 and related strains belonging to the same Paenibacillus sp. but not with that of other Bacillus spp. The four probes were cloned and sequenced to design specific primers for the biocontrol agent. Eight primers were designed, synthesized and tested with 23 strains mentioned above. The designed primers were strain specific and amplified only one band of PKB1. The specific primers will be used for the detection of this biological control agent in field studies to control diseases of canola.

VI. Inhibitory Effect of Strain PKB1 on Growth of *L. maculans* in Vitro and in Vivo Canola cultivars Quantum and Westar (*Brassica napus* L.) were grown in greenhouse pots for 2 weeks, sprayed with pycnidiospore suspension alone or mixed with the bacterial suspension, covered with a plastic bag to maintain high humidity for 2 days, and incubated at 20° C. in a greenhouse. Three and six weeks after incubation, disease severity was assessed using the scale of 0 to 5.

In greenhouse experiments, *Paenibacillus polymyxa* strain PKB1 significantly reduced blackleg incidence and severity on the susceptible cultivar Westar but not on the resistant cultivar Quantum (Table 4). '

TABLE 4

Effect of strain PKB1 on disease development caused by *Leptosphaeria maculans* (BLA) on canola plants in the greenhouse test.

| Cultivar | Treatment | Disease incidence | Disease severity |
|---|---|---|---|
| Westar | Sprayed with BLA pycnidiospore suspension | 100.0 a* | 3.64 a |
| Westar | Sprayed with BLA bacterial suspension | 59.6 b | 1.28 b |
| Quantum | Sprayed with BLA pycnidiospore suspension | 8.3 c | 0.08 c |
| Quantum | Sprayed with BLA bacterial suspension | 5.8 c | 0.06 c |

*Means followed by the same letter within rows are not significantly different according to LSD (P = 0.05)

VII. Effect of Tilt® and Strain PKB1 on Pycnidia Development, Pseudothecia Formation and Fungus Survival on Stubble At the 5-leaf stage, stems of *B. napus* cy Westar were inoculated at about 2 cm above the soil level using a mixture of two opposite strains of *L. maculans* capable of producing pseudothecia. About 6 weeks after inoculation, all plants were chopped leaving about 15 cm stubble above the soil level. All pots were then divided into three groups of 32 pots each; stubble in one of the groups was sprayed with Tilt® (active ingredient propiconazole)(@125 g a.i./ha)+ Adjuvant, another one was sprayed with the bacterial suspension ($7.4\times10^7$) whereas the third group served as an untreated check. Eight pots from each of the three groups were placed either for 10 weeks at one of the following temperatures: –5° C., 10° C., 20° C., or for two weeks at each of the following temperatures in succession, somewhat simulating an outdoor condition from fall to spring: 20° C., 10° C., –5° C., 10° C., 20° C. Out of the eight pots of each group at each temperature regime, four were covered with sterilized soil mix so as to cut-off light simulating soil-covered stubble. At each temperature regime, the arrangement of pots were completely randomized.

At the end of the 10 week period each stubble was rated for the blackleg severity using a 0–3 rating system (0=no pycnidia, 1=less than 10% area covered with pycnidia. 2=10 to 50% covered, and 3=more than 50% covered), and also checked for the presence of pseudothecia. Viability of *L. maculans* and of strain PKB1 present in the stem lesions and on the root system, was determined by culturing the tissue on an appropriate medium.

In the growth chamber test, stubbles treated with Tilt® had significantly fewer pycnidia than the corresponding untreated checks under all temperature regimes (except 20° C., unburied) (Table 5). Bacterium alone had minimal effect.

Strain PKB1 had profound effect on the viability of the fungus in the growth chamber (Table 5). Under most conditions, bacterium treated stubble had significantly lower survival of the fungus than the untreated check on those treated with Tilt®. This may be because strain PKB1 could grow inside the plant tissue and inhibit the growth of the fungus, whereas Tilt® could only inhibit the growth of the fungus on the surface of the plant tissue. The results suggest that strain PKB1 could significantly inhibit viability of *L. maculans* on canola stubble and thus reduce overall inoculum potential of the fungus.

TABLE 5

Occurrence of pycnidia and viability of *Leptosphaeria maculans* on canola stubble treated with Tilt ® or bacterium in a growth chamber, 1995.

| | Density of pycnidia on canola stubble | | | Mean number of infectious stubble[3] | | |
|---|---|---|---|---|---|---|
| Treatment | Tilt ® | Bacterium | Check | Tilt ® | Bacterium | Check |
| –5° C. | 0.25 a[1] | 1.00 b | 1.31 b | 4.19 a | 1.89 b | 4.19 a |
| –5° C. buried | 0.81 a | 1.29 a | 2.88 b | 3.38 a | 2.13 a | 3.44 a |
| 10° C. | 0.50 a | 1.66 b | 1.63 b | 4.13 b | 2.88 b | 4.94 b |
| 10° C. buried | 2.44 a | 2.92 b | 3.00 b | 3.31 a | 0.40 b | 4.00 a |
| 20° C. | 0.25 a | 0.71 b | 0.44 a | 4.75 a | 2.94 b | 4.56 a |
| 20° C. buried | 0.63 a | 0.84 ab | 1.75 b | 2.44 a | 0.18 b | 2.63 a |
| various T[2] | 0.44 a | 0.49 a | 1.06 b | 4.00 a | 4.25 a | 4.75 a |
| Various $T_2$ buried | 1.81 a | 1.31 ab | 2.31 b | 3.56 a | 1.13 b | 4.38 a |

[1]. Pycnidial density was evaluated on a scale of 0–3. Means followed by the same letter within rows are not significantly different according to LSD (P = 0.05).
[2]. Each sample was kept for 2 weeks at each of the five different temperatures, 20° C., 10° C., –5° C., 10° C., 20° C. in a cycle.
[3]. Values indicate the mean number of stubble pieces out of five yielding *L. maculans* colonies.

VIII. Effect of PKB1 on Other Pathogenic Fungi on Canola

Effectiveness of the *Paenibacillus polymyxa* strain PKB1 was tested against *Sclerotinia sclerotiorum, Rhizoctonia solani, Alternaria brassicae* and *Pythium pythioides* and *Fusarium* sp. Individual plates were inoculated with strain PKB1 and one of the test fungi. Zone of fungal inhibition was measured. The inhibitory effect was also tested in a liquid medium (potato dextrose broth) and the mycelium dry weight was collected after incubation.

In the petri plate test, strain PKB1 was found to have inhibitory effect on all the fungi tested. In the liquid culture also, significant inhibitory effect of the bacterial filtrate was observed on mycelial growth of all the fungi tested (Table 6). The results suggest that PKB1 has a potential of biological control not only against blackleg but also against other diseases of canola.

TABLE 6

Effect of strain PKB1 on mycelial growth of some pathogenic fungi of canola

| Pathogen | Mean mycelial dry weight (mg) | |
|---|---|---|
| | With bacterium | Control |
| *Sclerotinia sclerotiorum* | 5 a* | 152 b |
| *S. Sclerotiorum* | 3 a | 89 b |
| *Pythium pythioides* 88-1-8 | 16 a | 94 b |
| *Rhizoctonia solani* AG2-1 C51-25 | 13 a | 147 b |
| *R. solani* AG2-1 | 9 a | 153 b |
| *Fusarium avenaceum* N15-6 | 4 a | 53 b |
| *F. avenaceum* P66-30 | 3 a | 43 b |
| *Alternaria brassicae* | 3 a | 80 b |
| CA2 | 4 a | 21 b |

*Means of four replications; values in rows for each fungus followed by the same letter are not significantly different determined by LSD (P = 0.05).

IX. Effect of Fungicides and Herbicides on Strain PKB1

Effect of several fungicides and herbicides, registered for use on canola was determined on viability of the *Paenibacillus polymyxa* strain PKB1 in laboratory tests using 10-cm diameter petri plates containing PDA. A sterile filter paper disc, 1-cm diameter, dipped in one of the several chemical suspensions to be tested, was placed at the centre of each plate pre-seeded with strain PKB1. The chemicals included fungicides Tilt® (propiconazole), Sportak® (prochloraz) and Rovral® (iprodione) and the herbicides Lontrel® (clopyralid). Poast® (sethoxydim), and Muster® (ethametsulfuron). Clear zone of inhibition around the discs were measured.

All the herbicides and most of the fungicides tested were found to have no inhibitory effect on strain PKB1. Prochloraz® and Rovral® showed certain degree of inhibitory activity three days after the treatments, but it was overcome by strain PKB1 by the seventh day (Table 7). The results that the application of commonly used herbicides and fungicides on canola would not have deleterious effect on the survival of strain PKB1 in field.

TABLE 7

Measurement of the inhibition of strain PKB1 caused by different fungicides or herbicides.

| Treatment | Mean inhibition zone (mm) | |
|---|---|---|
| | Day 3 | Day 7 |
| Tilt ® | 1 | 0 |
| Rovral ® | 6 | 0 |
| Prochloraz ® | 7 | 1.5 |
| Poast ® | 0 | 0 |
| Muster ® | 0 | 0 |
| Lontrel ® | 0 | 0 |
| Control ® | 0 | 0 |

The bacterium, *Paenibacillus polymyxa* strain PKB1, has significant inhibitory effect on the growth and development of *Leptosphaeria maculans*.

The bacterium PKB1 is capable of inhibiting growth of different isolates of several fungi which cause important diseases on canola such as root rot, Sclerotinia stem rot and black spot.

Most chemicals used on canola do not have deleterious effect on the activity of the bacterium.

Tilt® significantly reduced number of pycnidia on stubble and bacterium significantly reduced survival of *L. maculans* under growth chamber condition.

Bacterial strains within a Paenibacillus species are more genetically related and distinguishable among the Bacillus species based on the DNA patterns. It is possible to detect the biocontrol agent PKB1 from other Paenibacillus species using DNA patterns by PCR-RAPD assay.

X. Blackleg Dose-response

To determine which concentrations (on a parts per million basis) of the pure *Paenibacillus polymyxa* antibiotic are effective in reducing mycelial dry weights of the blackleg fungus *Leptosphaeria maculans*, the following method is followed.

Pure *P. polymyxa* antibiotic is obtained according to example III and dried. An Eppendorf tube containing 721 ug of the dried, purified antibiotic is washed with 5 separate 1 ml aliquots of 70% methanol then taken to a volume of 70 ml which gave a stock solution of 10 ppm.

A pycnidiospore suspension of *L. maculans* is prepared by covering an actively sporulating plate of the fungus with sterile distilled water and scraping with a flame-sterilized glass hockey stick. A haemocytometer is used to determine a spore concentration of $5.5\times10^7$ spores/ml.

Potato dextrose broth (PDB) is prepared according to package directions and autoclaved at 121° C. for 25 minutes. After cooling, the broth is divided into 90 ml portions. The first 90 ml aliquot received 10 ml of the 10 ppm stock antibiotic solution to yield a 1 ppm solution of the antibiotic in PDB. This is shaken vigorously then 10 ml is removed and added to a second 90 ml aliquot of PDB to yield a 0.1 ppm solution of the antibiotic in PDB. This serial dilution is continued to give solutions if 0.01 ppm. 0.001 ppm and 0.0001 ppm of antibiotic in PDB. Controls consisted of plain PDB.

The PDB is then subdivided into small 60×15 mm Petri plates (10 ml per plate). Each concentration yielded 8 plates, 4 of which are inoculated with 10 ul of the pycnidiospore suspension of *L. maculans* while the remaining 4 received 100 ul of the spore suspension. Plates are placed on a rotary shaker (50 rpm) at room temperature until the development of mycelium occurred.

Whatman No. 1 filter papers (100 mm) are oven dried in a metal tray for 24 hours at 60° C. prior to harvesting the mycelium. Papers are weighed before harvest and the weight recorded. Mycelium is collected on the filter papers using a Buchner funnel under vacuum pressure. Filter papers are removed onto several layers of paper towel to remove excess liquid then paper-clipped to envelopes and placed in the dryer at 60° C. for 24 hours. Papers are fastened to envelopes to prevent them from being blown around in the dryer. After 24 hours, the papers are re-weighed and the weight of the mycelium calculated.

Plates are observed after 24 hours and after several days.

XI. *R. solani* Dose-response

To determine which concentrations (on a parts per million basis) of the *Paenibacillus polymyxa* antibiotic are effective in reducing mycelial dry weight of *Rhizoctonia solani* grown in a shake culture, the following method was followed.

Pure *P. polymyxa* antibiotic was obtained as in example III. An Eppendorf tube containing 721 ug of the dried, purified antibiotic was washed with 5 separate 1 ml aliquots of 70% methanol then taken to a volume of 70 ml which gave a stock solution of 10 ppm.

*Rhizoctonia inoculum* was prepared by scraping mycelium from the surface of an agar plate with a flame-sterilized scalpel. The mycelium was placed in a manual tissue macerator in 5 ml of sterile distilled water and ground until the solution was consistently cloudy and there were no large clumps of mycelium.

Potato dextrose broth (PDB) was prepared according to package directions and autoclaved at 121° C. for 25 minutes. After cooling, the broth was divided into 90 ml portions. The first 90 ml aliquot received 10 ml of the 10 ppm stock antibiotic solution to yield a 1 ppm solution of the antibiotic in PDB. This was shaken vigorously then 10 ml was removed and added to a second 90 ml aliquot of PDB to yield a 0.1 ppm solution of the antibiotic in PDB. This serial dilution was continued to give solutions of 0.01 ppm, 0.001 ppm and 0.0001 ppm of antibiotic in PDB. Controls consisted of plain PDB.

The PDB was then subdivided into small 60×15 mm Petri plates (100 ml per plate). Each concentration yielded 4 plates which were each inoculated with 100 ul of the Rhizoctonia macerate. Plates were sealed and placed on a rotary shaker (50 rpm) at room temperature until the development of mycelium occurred.

Whatman No. 1 filter papers (100 mm) were oven dried in a metal tray for 24 hours at 60° C. prior to harvesting the mycelium. Papers were weighed before harvest and the weight recorded. Mycelium was collected on the filter papers using a Buchner funnel under vacuum pressure. Filter papers were removed onto several layers of paper towel to remove excess liquid then paper-clipped to envelopes and placed in the dryer at 60° C. for 24 hours. Papers were fastened to envelopes to prevent them from being blown around in the dryer. After 24 hours, the papers were re-weighed and the weight of the mycelium calculated.

Whereas the dose-response with blackleg showed mycelial growth within 24 hours of inoculation, the Rhizoctonia grew much more slowly, needing over a week before mycelium was noticed. Growth responses were recorded after 12 days of growth on a +/− scale in Table 9. The number of "+" symbols indicates the relative amount of mycelium seen.

TABLE 9

Growth response of Rhizoctonia to various levels of antibiotic incorporated into PDB.

| Treatment | Presence of Mycelium | | | |
|---|---|---|---|---|
| | Rep 1 | Rep 2 | Rep 3 | Rep 4 |
| 0 ppm | ++ | +++ | +++ | +++ |
| 0.0001 ppm | +++ | +++ | +++ | +++ |
| 0.001 ppm | ++ | ++ | + | + |
| 0.01 ppm | + | + | − | ++ |
| 0.1 ppm | − | + | + | + |
| 1.0 ppm | − | − | − | − |

Mycelium was harvested 16 days after the start of the experiment. An ANOVA test run on the data indicated a significant concentration effect. Table 10 contains the mean mycelial dry weights for each treatment as well as the Tukey separations.

TABLE 10

Mean mycelial dry weights of Rhizoctonia grown in PDB amended with various concentrations of antibiotic.

| Treatment | Mean Mycelial Dry Weight (g) |
|---|---|
| 0 ppm | 0.0614 ± 0.00108 ab |
| 0.0001 ppm | 0.0635 ± 0.0085 a |
| 0.001 ppm | 0.0336 ± 0.00148 bc |
| 0.01 ppm | 0.0411 ± 0.0231 abc |
| 0.1 ppm | 0.0146 ± 0.0005 c |
| 1.0 ppm | 0.0136 ± 0.0007 c |

Weights represent the mean of 4 replicates, 1 plate per replicate. Means followed by the same letter are not significantly different at $P<0.05$.

Data in Table 10 suggests that the 0.1 and 1.0 ppm levels of antibiotic are responsible for a significant reduction in mycelial dry weight of Rhizoctonia.

XII. Development of Antibiotic-resistant PKB1 Mutants

Single bacterial colonies of *P. polymyxa* PKB1 were transferred to potato dextrose agar (PDA) plates amended with the antibiotics rifampicin (10 mgoL−1, 50 mgoL−1 and 100 mgoL−1), nalidixic acid (10 mgoL−1), or rifampicin+nalidixic acid (10 mgoL−1 each). The surviving colonies were subsequently transferred to antibiotic amended PDA plates for 10 generations to confirm stability of the antibiotic resistant mutants.

Fifteen resistant mutants were obtained using a continuous selection procedure (Table 11). The mutant cells were freeze-dried and kept in a freezer for later use.

TABLE 11

List of selected antibiotic resistant mutants of PKB1 (*Paenibacillus polymyxa*).

| Strain | Code | Description |
|---|---|---|
| 97-001 | R1 | Resistant to rifampicin 100 mg/L |
| 97-002 | R1X | Resistant to rifampicin 100 mg/L, dark pink, glossy, raised |
| 97-003 | R1Y | Resistant to rifampicin 100 mg/L, light cream/pink, flat |
| 97-004 | R1Z | Resistant to rifampicin 100 mg/L, dark pink, raised, more glossy |
| 97-005 | R2 | Resistant to rifampicin 100 mg/L |
| 97-006 | R2a | Resistant to rifampicin 100 mg/L, lighter colony color |
| 97-007 | R2b | Resistant to rifampicin 100 mg/L, darker colony color |
| 97-008 | R2a100 | Resistant to rifampicin 100 mg/L, slower growth |
| 97-009 | R3b50 | Resistant to rifampicin 100 mg/L |
| 97-010 | R3b100 | Resistant to rifampicin 100 mg/L |
| 97-011 | NIN on RN10 | Resistant to rifampicin 100 mg/L + nalidixic acid (10 mg/L) |
| 97-012 | NIRNA ON RN10 | Resistant to rifampicin 100 mg/L + nalidixic acid (10 mg/L) |
| 97-013 | NIRNB ON RN10 | Resistant to rifampicin 100 mg/L + nalidixic acid (10 mg/L) |
| 97-014 | R2RNA ON RN10 | Resistant to rifampicin 100 mg/L + nalidixic acid (10 mg/L) |
| 97-015 | R2RNB ON RN10 | Resistant to rifampicin 100 mg/L + nalidixic acid (10 mg/L) |

XIII. Development of Specific Primers for the Biocontrol Agent

DNA cloning and sequencing: Four DNA probes were cloned on *Escherichia coli* supercompetent cells using a pCR-Script™ SK(+) Cloning Kit (Stratagene). Plasmid DNA was extracted using a PlasmidPURE™ DNA Miniprep Kit (Sigma Bio Sciences™) following the supplier's instructions.

Confirmed plasmid DNA with insert was sequenced using a DNA sequencing machine (ABI Prism). Two universal primers T3 and T7 were used. The data were edited and analyzed using a computer software GeneJockey®.

DNA fragments of four probes were cloned and sequenced. The length of the fragments was found to be 609 bp (P1–7), 713 bp (P1–8), 270 bp (P1–13) and 617 bp (P1–14). Sequences P1–8 and P1–7 could be translated with no or few stops in some reading frames. Sequence P1–8 (FIG. 11 and SEQ ID NO:6) has 67% identity in reading frame 3 with the gene (spo0E) of a protein required to initiate sporulation in *Bacillus subtilis*. The other (P1–7, RF6) has 31% identity in reading frame 6 with an enzyme produced by a Bacillus sp. Designing and developing specific primers for PKB1 according to the DNA sequences were conducted.

Development of specific primers: DNA sequences were entered into GeneJockey® and searched for possible primers. Eight compatible primers were designed using Amplifiers® software. The three best primers are shown in Table 12. Primers were synthesized according to the indicated sequences and examined in PCR reactions with 23 Bacillus and Paenibacillus strains for specificity to PKB1.

TABLE 12

Primers designed from DNA sequences.

| Primer | Source | Sequence |
|---|---|---|
| J1 | P1-8 | 5'-AGCGTCAACGGATTGGCATAGC |
| JY1 | P1-8 | 5'-CTATTCCTGAGCCACCTGCTTATGC |
| JY2 | P1-8 | 5'-GTTCATCTATTCCTGAGCCACCTGC |

In the attached Sequence Listing, primer J1 is listed as SEQ ID NO:9, primer JY1 is listed as SEQ ID NO:10 and primer JY2 is listed as SEQ ID NO:8.

RFLP analysis of the PCR products amplified with primers J1 and JY1 from 10 bacterial strains was conducted with three restriction endonucleases, RsaI, MseI, and Sau3AI to check the polymorphism on the restriction site of these 10 bacteria. The reaction mix contained 2 μl DNA of the PCR product, 1 μl (5 units) restriction endonuclease, 2 μl reaction buffer and 15 μl water. The reaction was carried out in a 37° C. water bath for 1 h. The digests were separated on 1.5% agarose gel at 100 V. The gel was stained with ethidium bromide and photographed under UV light.

Detection of PKB1 with specific primers—The eight primers designed, three of which are shown in Table 12, had ten primer pair combinations. At 55 ° C. annealing temperature, six primers with eight pairs gave similar results and amplified only one DNA band (about 500 bp) of PKB1 (lane 1) and other related strains (lanes 2–8) from the same geographical area, but not in other strains in the same species and strains of other Paenibacillus and Bacillus spp. (FIG. 12). Two *P. polymyxa* strains (97-2, lane 9 and 97-3, lane 10 in FIG. 12) did not have inhibitory effect against *L. maculans* and they could not be amplified with any pair of these specific primers. DNA of two bacterial strains (97-4, lane 11 and 96–9, lane 12 in FIG. 12) that had no inhibitory effect to *L. maculans* but were inhibitory to *Rhizocionia solani* and other pathogens could also be amplified with these designed primers. One strain of Erwinia sp. that was also included in the PCR test did not yield any PCR product.

The result showed that primers J1, JY1 and JY2 were partially strain specific and could be used for detection of this biocontrol agent during field trail studies. Thirteen *P. polymyxa* strains were divided into two subgroups based on these primers. The first group includes all strains that could be amplified by the primers, and the second one includes 97-2 and 97-3 that could not be amplified.

To further distinguish these strains in the first group of *P. polymyxa*, the DNA fragments (513 bp) of 96-1 (#1, lane 2 in FIG. 12) and 97-4 (#11, lane 12 in FIG. 12) from the same PCR reaction amplified with the designed primers (J1 and JY1) were purified and sequenced in a DNA sequencer (Applied Biosystems/Perkin Elmer 373). DNA fragments of PKB1 and 97-4 amplified with J1 and JY1 differed in only one base.

A complete restriction map was generated for the DNA fragment of PKB1 (#1, lane 1 in FIG. 12) and 97-4 (#11; lane 12 in FIG. 12), respectively, using DNA Strider™ 1.2 computer software. These two DNA fragments differed in one restriction endonuclease site, Tth111 II site was absent in strains 96-9 and 97-4. Because this enzyme (Tth111 II) is not commercially available at the present time, the RFLP procedure could not be conducted. However, this enzyme should prove to be a useful marker for differentiating PKB1 from other non-anti-blackleg *P. polymyxa* strains based on the RFLP pattern once it becomes commercially available.

XVI. Effect of PKB1 for Biological Control of Fairy Ring in the Turfgrass in Vitro Further experimentation was directed towards controlling fairy rings in turfgrass caused by *Marasmius oreades.*

Two *M. oreades* isolates (one from gill and one from stipe) were obtained from a fungal mushroom collected from a fairy ring in the Vegreville, Alberta, Canada area. The fungal cultures were grown in Malt-potato dextrose agar (MPDA) and kept at a temperature of 4° C.

A 5-mm diameter MPDA plug containing *M. oreades* mycelium was placed onto a PDA plate and 10 μl drops of a spore suspension of an antibiotic resistant mutant of the bacterium *P. polymyxa* strain PKB1 (97-006) were spotted onto the plug. Plates without bacterial inoculation were used as controls. Four plates were inoculated for each fungal isolate (gill and stipe) and each treatment (bacterial treated and control without bacterium). The 16 plates were randomly placed in an incubator at 20° C. for 7 days. The diameter of fungal colony was measured to determine the effect of the bacterium on the inhibition of the fungal growth on the MPDA. Four random measurements were made for each colony.

The bacterial mutant strain 97-006 significantly inhibited the mycelial growth of both isolates of *M. oreades* (Table 13). The colony diameter of the fungus co-inoculated with the bacterium was significantly reduced.

TABLE 13

Inhibitory effect of a bacterium mutant
strain 97-006 on growth of *Marasmius oreades* in vitro.

| Treatment | Culture | Mean Colony Diameter (mm) |
| --- | --- | --- |
| 97-006 | Gill | 5.75 a* |
| CK | Gill | 42.44 b |
| 97-006 | Stipe | 7.19 a |
| CK | Stipe | 35.88 b |

*Means of 16 measurements. Means followed by the same letter are not significantly different according to Duncan's Multiple

XIV. Development of Disease Suppressive Composts Using *P. polymyxa* PKB1

XIV.i. Preparation of Compost:

The composts were prepared under the supervision of the Compost Technology Centre (CTC), Olds, Alberta, Canada. Mature and near mature composts (cattle manure and wood chips) were pasteurized by steaming 0.5 m$^3$ of each for 5 hours at 80° C. in a soil steamer to destroy the resident microorganisms, thus enhancing the effectiveness and viability of the intended PKB1 spore inoculum. After cooling to 45° C., 0.25 m$^3$ of each material was spread out in layers, and soybean meal and/or spores of the bacterium were added and well mixed with the compost. The spore suspension (1×10$^9$ cfu/ml) was prepared in distilled water (pH 7.4) from the freeze-dried spores. The suspension was further diluted to 3.7–4.2×10$^6$ cfu/ml.

The inoculated composts were incubated in 0.25 m$^3$ commercial composters to enhance the population of PKB1. The two soybean meal supplemented portions were incubated in forced aeration composters and without aeration in passive aeration composters.

Ten cubic meters of cattle manure and wood chips, which had been composting for three months, was isolated and intensively turned to enhance the oxygen concentration, bringing the material to the beginning of the maturing phase. When the oxygen concentration reached ~18% indicating the start of the maturing phase, 1 m$^3$ of the material was steam pasteurized at 80° C. for 5 hours and then left to cool to 40° C. in the steam wagon.

To half of this material (Bulk density 539.8 kg/m$^3$), 13.5 kg of soybean meal (5%m/m) was added and well mixed in. 18.91 g of freeze dried spore preparation (4.7×10$^{10}$ cfu/mg) was dispersed in 1 L of distilled water and the suspension made up to 3.785 L and sprayed evenly over this half of the pasteurized compost. The resultant inoculum concentration was 3.3×10$^9$ cfu/g dry mass of compost.

The control half of the pasteurized compost had only the 13.5 kg soybean meal added. Two 0.25 m$^3$ compost bins were filled with material from each treatment and incubated with forced aeration. Temperature, oxygen concentration, moisture and pH were monitored.

Within two weeks the average temperature of the initial material had dropped by 10° C. and the oxygen concentration rose from 4 to 18% indicating the start of the maturing phase. pH measured 7.5 and moisture was 41.7%.

During incubation of the composts, all bins show an immediate increase in temperature and a precipitous drop in oxygen concentration as a result of the utilization of the nitrogenous soybean meal. The spore containing bins show a more vigorous reaction than the control bins with higher temperatures and quicker depletion of the added protein substrate demonstrated by the quicker return to a higher oxygen concentration. This is due to a larger viable population in the spore spiked bins after the steam pasteurization treatment.

The pH of the material rises to ~8 because of the added soybean meal.

The material was harvested after 27 days of incubation and stored in jute bags. At weekly intervals during the composting period, samples were taken for spore enumeration and pathogen inhibiting assessment.

XIV.ii. Assessment of Strain PKB1 in Compost

In vitro assessment: One gram (wet weight) of each compost sample was placed in dilution buffer and then heated to 80° C. for 30 min to kill any vegetative cells and non-spore forming bacteria. Dilution series (10 fold) were made and then 0.1 ml of each dilution was plated onto PDA plates. Bacterial colonies were counted after 48 h incubation at 22° C. The replicas of bacterial colonies on PDA plates were made on to PDA+rifampicin (100 mg·L$^{-1}$) plates and incubated at 25° C. for 48 h and the final counts were determined per gram wet weight of the compost.

The inhibitory effect of PKB1 re-isolated from compost was confirmed by using two methods. In the first, a loop of the bacterium was placed at four places on a PDA plate, around an agar plug of *L. maculans* culture. Inhibition zones in the culture around the bacterial colonies were checked after 10 days incubation at 22° C. In the second, 0.1 ml of the diluted compost suspension and 0.9 ml of *L. maculans* spore suspension were mixed and then spread onto four PDA plates. Inhibition of fungal growth was observed after one week of incubation at room temperature.

The concentration of bacteria in composts inoculated with strain PKB1 and compost without bacterial inoculation ranged from 2.0×10$^7$ to 3.4×10$^8$ on PDA plates. To confirm that the uninoculated compost did not contain PKB1 mutant, we tested the bacterial colonies isolated above on PDA amended with rifampicin. Very few bacterial colonies from compost without inoculum survived on rifampicin amended plates. The results showed that the antibiotic resistance was a suitable marker for detecting the bacterium from compost. Subsequent incubation or rifampicin-amended PDA indicated that #97-003 recovered from compost was strongly inhibitory to *L. maculans* mycelial growth (FIG. 13). Most bacteria recovered from non-inoculated compost had no effect on the blackleg isolate.

XV. Effect of Compost-bacterium on *Sclerotinia sclerotiorum* in Growth Chamber Tests An isolate of *Sclerotinia sclerotiorum* was cultured on potato-dextrose agar plates for one week under light at room temperature. After sclerotia had formed on the agar, the plates were moved to an incubator and incubated at 10° C. in the dark for five weeks. The sclerotia were then harvested and used in growth chamber tests. Two experiments were conducted.

In the first experiment, composts containing PKB1 were mixed with greenhouse soil (1:1, v:v) and filled in 10-cm fiber pots. Five sclerotia were buried in the mixture and incubated in a growth chamber at a constant temperature of 20° C. with 12 h light. The pots were kept moist for the duration of the experiment. Pots without compost-bacterium were used as controls. There were four replications for each treatment. Germinated sclerotia and the number of apothecia formed were counted three weeks after seeding; counting was repeated at 10-day interval for another 30 days.

In the second experiment, 10-cm pots were filled with compost containing PKB1 antibiotic resistant mutant (97-003) or compost alone. In addition, the compost was used without any ProMix or greenhouse soil. Ten sclerotia were buried in the compost and incubated in a growth chamber programmed at the same settings used in the first experiment. Pots with ProMix growth medium were used as controls. There were five replications for each treatment. Germinated sclerotia and the number of apothecia formed were counted three weeks after seeding, and counted again at 7 day intervals for another 21 days.

In experiment one, compost (C4)+bacterium significantly inhibited germination of sclerotia of *S. sclerotiorum* three weeks after inoculation compared to the control (Table 14), whereas the other compost treatments had no significant effect. Also, the number of apothecia in compost C4 was the least compared with other composts. Some of the batches of composts did not have significant effect. Total number of viable bacterial cells in these batches was found to be quite low. This suggests that the substrate of the compost may influence the success of establishment and overall performance of strain PKB1.

In experiment two, where compost was not mixed with any greenhouse soil or ProMix, compost or compost+ bacterium completely inhibited the germination of sclerotia. In the control treatment (sclerotia buried in ProMix), 58% of sclerotia germinated and produced apothecia.

TABLE 14

Effect of compost + bacterium on germination of sclerotia of *Sclerotinia sclerotiorum* tested in a growth chamber.

| Compost | Number of Germinated Sclerotia | Number of Apothecia |
| --- | --- | --- |
| C1 | 3.75 a* | 7.50 a |
| C2 | 2.50 ab | 5.00 ab |
| C3 | 3.75 a | 5.50 ab |
| C4 | 1.00 b | 1.75 b |
| C5 | 2.00 ab | 3.00 ab |
| C6 | 2.50 ab | 4.00 ab |
| C7 | 3.25 a | 4.25 ab |
| CK | 3.75 a | 5.00 ab |

*Means in a column followed by the same letter are not significantly different as determined by a Duncan's multiple Range Test (P = 0.05).

It will be apparent that many other changes may be made to the illustrative embodiments, while falling within the scope of the invention and it is intended that all such changes be covered by the claims appended hereto.

---

The embodiments of the invention in which an exclusive property or privilege is claimed are defined as follows:

1. A biologically pure *Paenibacillus polymyxa* strain ATCC 202127 capable of producing a peptide antibiotic against Leptosphaeria spp. or mutants of said strain capable of producing said peptid.

2. The biologically pure *Paenibacillus polymyxa* strain or mutants of said strain of claim 1, wherein the Leptosphaeria spp. is *Leptosphaeria maculans.*

3. The biologically pure *Paenibacillus polymyxa* strain or mutants of said strain of claim 1, modified to have antibiotic resistance.

4. The biologically pure *Paenibacillus polymyxa* strain or mutants of said strain of claim 3, capable of producing a peptide antibiotic against a fungus selected from the group consisting of Sclerotinia spp., Rhizoctonia spp., Pythium spp., Fusarium spp., Alternaria spp., Aspergillus spp., Sporobolomyces spp., Trichoderma spp., Penicillium spp. or Marasmius spp.

5. The biologically pure *Paenibacillus polymyxa* strain or mutants of said strain of claim 1, in a compost.

6. The biologically pure *Paenibacillus polymyxa* strain or mutants of said strain of claim 1, in a compost.

7. The biologically pure *Paenibacillus polymyxa* strain or mutants of said strain of claim 1, capable of inhibiting growth of Micrococcus spp., Streptomyces spp. or Escherichia spp.

8. A method of controlling a fungal disease of a crop comprising:

applying an amount of *Paenibacillus polymyxa* strain ATCC 202127 capable of producing a peptide antibiotic against fungi or mutants of said strain capable of producing said peptide, to at least one of a) a medium in which the crop will be grown, b) of the crop prior to planting the crop, and c) plants of the crop.

9. The method of claim 8, wherein the *Paenibacillus polymyxa* strain or mutants of said strain are in the vegetative state.

10. The method of claim 8, wherein the *Paenibacillus polymyxa* strain or mutants of said strain are in the spore stage.

11. The method of claim 8, wherein the amount of the *Paenibacillus polymyxa* strain or mutants of said strain contains some *Paenibacillus polymyxa* spores.

12. The method of claim 8, wherein the *Paenibacillus polymyxa* strain or mutants of said strain are dried.

13. The method of claim 8, further comprising applying in addition to said strain or mutants of said strain, an amount of fungicide to at least one of a) a medium in which the crop will be grown, b) seeds of the crop prior to planting, and c) plants of the crop.

14. The method of claim 8, wherein the amount of the *Paenibacillus polymyxa* strain or mutants of said strain, is included in compost material.

15. The method of claim 8, wherein the disease is caused by *Leptosphaeria maculans.*

16. The method of claim 8, wherein the disease is caused by a fungus selected from the group consisting of Leptosphaeria spp., Sclerotinia spp., Rhizoctonia spp., Pythium spp., Fusarium spp., Alternaria spp., Aspergillus spp., Sporobolomyces spp., Trichoderma spp., Penicillium spp. and Marasmius spp.

* * * * *

UNITED STATES PATENT AND TRADEMARK OFFICE
CERTIFICATE OF CORRECTION

PATENT NO.   : 6,602,500 B1
DATED        : August 5, 2003
INVENTOR(S)  : Kharbanda et al.

It is certified that error appears in the above-identified patent and that said Letters Patent is hereby corrected as shown below:

Column 39,
Line 43, "peptid" reads -- peptide --;
Line 51, claim 4 depends from claim 1;
Line 60, claim 6 depends from claim 4;

Column 40,
Line 39, the word -- seeds -- is inserted after "b)"

Signed and Sealed this

Twenty-third Day of December, 2003

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 1
gagctctaga attcagagtt tgatcatggc tcag         34

<210> SEQ ID NO 2
<211> LENGTH: 23
<212> TYPE: DNA
<213> ORGANISM: Artificial sequence
<220> FEATURE:
<223> OTHER INFORMATION: Description for Artificial Sequence:  primer

<400> SEQUENCE: 2
tgtgtagcgg tgaaatgcgt aga         23

<210> SEQ ID NO 3
<211> LENGTH: 19
<212> TYPE: DNA
<213> ORGANISM: Artificial sequence
<220> FEATURE:
<223> OTHER INFORMATION: Description for Artificial Sequence: primer

<400> SEQUENCE: 3
aggaaggggg ggaggaggt                                                    19

<210> SEQ ID NO 4
<211> LENGTH: 19
<212> TYPE: DNA
<213> ORGANISM: Artificial sequence
<220> FEATURE:
<223> OTHER INFORMATION: Description for Artificial Sequence: primer

<400> SEQUENCE: 4
cccactggtg cctcccgta                                                    19

<210> SEQ ID NO 5
<211> LENGTH: 22
<212> TYPE: DNA
<213> ORGANISM: Artificial sequence
<220> FEATURE:
<223> OTHER INFORMATION: Description for Artificial Sequence: primer

<400> SEQUENCE: 5
cgcccttttc gggacttaac cc                                                22

<210> SEQ ID NO 6
<211> LENGTH: 713
<212> TYPE: DNA
<213> ORGANISM: Artificial sequence
<220> FEATURE:
<223> OTHER INFORMATION: Description for Artificial Sequence: probe

<400> SEQUENCE: 6
gtgacgtagg gttaggcgcg catttagcgg atcggcatcc ccatgaattc agtggcgggc        60
agcgtcaacg gattggcata gcgagagcac tggctatgaa accgaagctc attgtttgtg       120
atgaacctgt atccgcgctg gatgtgtcaa ttcaggctca gattttgaat ttgttaaagg       180
agcttcagca gcagttccag cttacctaca tttttattgc ccacggggttg ccctccgtca      240 agcatattag cgaccgcatc gcggtgatgt acttgggcaa aatcgtggag cttgcagatc       300
gtgacgagtt gtttgcaaga ccgcaacatc cgtatacaaa agcattgctt gaggcagtgc       360
ctgttcctga tccgaggttg cgtataagaa cggatcacat tgacggggga aatccccaat       420
cccgccaatc cgccttcggg ctgtactttt cacacgcgtt gccctatgc acaagagata       480 tgccgactac agagtccatt gctcgaagag catactccag gacatattgc tgcctgtcat       540
tttcccctgc ataagcaggt ggctcaggaa tagatgaact tttggaagta ggcgttaacc       600
aaaaaaagga ggctactcat gaataaacga tcaattgtac cggaggattt gtacggatat       660
cagtggatca gtgatcccac aataagcccc gatgaacga ttgcctacgt cac              713

<210> SEQ ID NO 7
<211> LENGTH: 34
<212> TYPE: DNA
<213> ORGANISM: Artificial sequence
<220> FEATURE:
<223> OTHER INFORMATION: Description for Artificial Sequence: primer -continued

```
<400> SEQUENCE: 7
tcgagctcta gaattcgggc ggtgtgtaca aggc                              34

<210> SEQ ID NO 8
<211> LENGTH: 25
<212> TYPE: DNA
<213> ORGANISM: Artificial sequence
<220> FEATURE:
<223> OTHER INFORMATION: Description for Artificial Sequence: primer

<400> SEQUENCE: 8
gttcatctat tcctgagcca cctgc                                       25

<210> SEQ ID NO 9
<211> LENGTH: 22
<212> TYPE: DNA
<213> ORGANISM: Artificial sequence
<220> FEATURE:
<223> OTHER INFORMATION: Description for Artificial Sequence: primer

<400> SEQUENCE: 9
agcgtcaacg gattggcata gc                                          22

<210> SEQ ID NO 10
<211> LENGTH: 25
<212> TYPE: DNA
<213> ORGANISM: Artificial sequence
<220> FEATURE:
<223> OTHER INFORMATION: Description for Artificial Sequence: primer

<400> SEQUENCE: 10
ctattcctga gccacctgct tatgc                                       25
```